US012753157B2

(12) United States Patent
Kamimura et al.

(10) Patent No.: US 12,753,157 B2
(45) Date of Patent: Oct. 6, 2026

(54) AMINIMIDE COMPOUND, AMINIMIDE COMPOSITION, CURING AGENT, EPOXY RESIN COMPOSITION, METHOD FOR PRODUCING AMINIMIDE COMPOUND, ENCAPSULANT, AND ADHESIVE

(71) Applicant: ASAHI KASEI KABUSHIKI KAISHA, Tokyo (JP)

(72) Inventors: Naoya Kamimura, Tokyo (JP); Teruhisa Yamada, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 741 days.

(21) Appl. No.: 18/016,182

(22) PCT Filed: Jul. 14, 2021

(86) PCT No.: PCT/JP2021/026500
§ 371 (c)(1),
(2) Date: Jan. 13, 2023

(87) PCT Pub. No.: WO2022/014646
PCT Pub. Date: Jan. 20, 2022

(65) Prior Publication Data

US 2023/0212132 A1 Jul. 6, 2023

(30) Foreign Application Priority Data

Jul. 15, 2020 (JP) ................................ 2020-121122

(51) Int. Cl.
*C09J 11/06* (2006.01)
*C07D 295/32* (2006.01)
*C09J 163/00* (2006.01)

(52) U.S. Cl.
CPC ............ *C07D 295/32* (2013.01); *C09J 11/06* (2013.01); *C09J 163/00* (2013.01); *C09J 2463/00* (2013.01)

(58) Field of Classification Search
CPC .............................. C09L 11/06; C07D 295/32
See application file for complete search history.

(56) References Cited

U.S. PATENT DOCUMENTS

| | | | |
|---|---|---|---|
| 3,888,827 | A | 6/1975 | Matueda et al. |
| 3,985,793 | A | 10/1976 | Brooks et al. |
| 4,005,055 | A | 1/1977 | Miron et al. |
| 2010/0253213 | A1 | 10/2010 | Tamatani et al. |
| 2012/0095124 | A1 | 4/2012 | Kirino |
| 2017/0166686 | A1 | 6/2017 | Zhou et al. |

FOREIGN PATENT DOCUMENTS

| | | | | |
|---|---|---|---|---|
| JP | 48-43089 B1 | | 12/1973 | |
| JP | 49-74799 | * | 7/1974 | C07C 241/00 |
| JP | 49-74799 A | | 7/1974 | |
| JP | 49-127911 A | | 12/1974 | |
| JP | 50-76199 | * | 6/1975 | C07C 241/00 |
| JP | 50-76199 A | | 8/1975 | |
| JP | 50-100020 A | | 8/1975 | |

(Continued)

OTHER PUBLICATIONS

Hideki Niino et al., J'nal of Applied Polymer Sci., vol. 27 (1982) pp. 2361-2368.*
Haywood et al., J'nal of Fluorine Chem. (1991) vol. 51, pp. 419-431.*
Cas(STN) Reg STN 2004 791721-38-5.*
"7,10-Dioxa-2,15-diaza-3,14-diazoniaheptacosane, 5,12-dihydroxy-3,3,14,14-tetramethyl-2,16-dioxo-1-phenyl-(CA Index Name)," Registry (STN) [online], CAS Registry: 791721-38-5, etc., 2004, XP055898630, 17 pages total.
English translation of the International Search Report for International Application No. PCT/JP2021/026500, dated Sep. 14, 2021.

(Continued)

*Primary Examiner* — Paul V Ward
(74) *Attorney, Agent, or Firm* — Birch, Stewart, Kolasch & Birch, LLP

(57) ABSTRACT

Provided is an aminimide compound that is excellent in penetration and has excellent curability and storage stability. An aminimide compound represented by the following formula (1), (2) or (3):

(1)

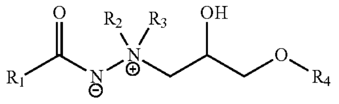

(2)

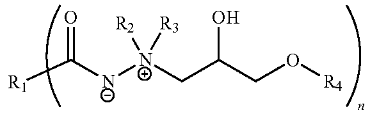

(3)

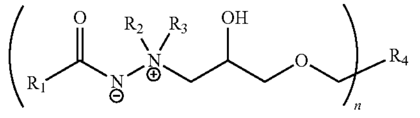

wherein each $R_1$ independently represents a hydrogen atom, or a monovalent or n-valent organic group having 1 to 15 carbon atoms and optionally having a hydroxy group, a carbonyl group, an ester bond, or an ether bond; $R_2$ and $R_3$ each independently represent an unsubstituted or substituted alkyl group having 1 to 12 carbon atoms, aryl group, aralkyl group, or heterocyclic ring having 7 or less carbon atoms in which $R_2$ and $R_3$ are linked to each other; each $R_4$ independently represents a hydrogen atom, or a monovalent or n-valent organic group having 1 to 30 carbon atoms and optionally containing an oxygen atom; and n represents an integer of 1 to 3.

20 Claims, No Drawings

(56) References Cited

FOREIGN PATENT DOCUMENTS

| | | | | | |
|---|---|---|---|---|---|
| JP | 61-231020 | * | 10/1986 | .......... | C07C 241/00 |
| JP | 61-231020 | A | 10/1986 | | |
| JP | 1-242132 | * | 9/1989 | .......... | C07C 241/00 |
| JP | 1-242132 | A | 9/1989 | | |
| JP | 1-304033 | A | 12/1989 | | |
| JP | 2-145677 | * | 6/1990 | .......... | C07C 241/00 |
| JP | 2-145677 | A | 6/1990 | | |
| JP | 2000-229927 | * | 8/2000 | .......... | C07C 241/00 |
| JP | 2000-229927 | A | 8/2000 | | |
| JP | 2000-309686 | A | 11/2000 | | |
| JP | 2000-340720 | A | 12/2000 | | |
| JP | 2003-055638 | * | 2/2003 | .......... | C07C 241/00 |
| JP | 2003-55638 | A | 2/2003 | | |
| JP | 2003-096061 | * | 4/2003 | .......... | C07C 241/00 |
| JP | 2003-96061 | A | 4/2003 | | |
| JP | 2004-284955 | A | 10/2004 | | |
| JP | 2008-1857 | * | 1/2008 | .......... | C07C 241/00 |
| JP | 2008-1857 | A | 1/2008 | | |
| JP | 2009-120683 | * | 6/2009 | .......... | C07C 241/00 |
| JP | 2009-120683 | A | 6/2009 | | |
| JP | 6282515 | B2 | 2/2018 | | |
| WO | WO 2009/084229 | A1 | 7/2009 | | |
| WO | WO 2010/147161 | A1 | 12/2010 | | |

OTHER PUBLICATIONS

Haywood et al., "Amine(Polyfluoroalkoxyacyl)imide Surfactants [1]," Journal of Fluorine Chemistry, vol. 51, 1991, pp. 419-431.

International Preliminary Report on Patentability and English translation of the Written Opinion of the International Searching Authority for International Application No. PCT/JP2021/026500, dated Jan. 26, 2023.

Niino et al., "Aminimide as Hardener/Curing Promotor for One Part Epoxy Resin Composition," Journal of Applied Polymer Science, vol. 27, 1982, pp. 2361-2368.

* cited by examiner

AMINIMIDE COMPOUND, AMINIMIDE COMPOSITION, CURING AGENT, EPOXY RESIN COMPOSITION, METHOD FOR PRODUCING AMINIMIDE COMPOUND, ENCAPSULANT, AND ADHESIVE

TECHNICAL FIELD

The present invention relates to an aminimide compound, an aminimide composition, a curing agent, an epoxy resin composition, a method for producing an aminimide compound, an encapsulant, and an adhesive.

BACKGROUND ART

Epoxy resin has heretofore been used in a wide range of applications such as coating materials, electric or electronic insulating materials, and adhesives because its cured product has excellent performance in terms of mechanical characteristics, electric characteristics, thermal characteristics, chemical resistance, adhesion, and the like.

Current epoxy resin compositions generally used are so-called two-component epoxy resin compositions in which two components, epoxy resin and a curing agent, are mixed when used.

The two-component epoxy resin compositions are capable of being cured at room temperature, whereas their problems are that: storage or handling is complicated because the epoxy resin and the curing agent need to be separately stored and weighed and mixed each time they are used; and these components cannot be mixed in advance in large amounts due to a limited available time.

Some one-component epoxy resin compositions have been proposed so far (see, for example, Patent Documents 1 to 3) for the purpose of solving the problems of the two-component epoxy resin compositions as mentioned above. Examples thereof include epoxy resin compositions containing a latent curing agent blended with epoxy resin.

There are requirements including downsizing, high functionality, lightening, high functionality, and multifunctionality for current electronic devices. For example, semiconductor chip packaging techniques are also required to attain further miniaturization, downsizing, and high densification brought about by finer pitches of electrode pads and pad pitches. Hence, underfills as adhesives for use in the space between chips and substrates are required to penetrate narrower gaps.

CITATION LIST

Patent Document

Patent Document 1: Japanese Patent No. 6282515

Patent Document 2: Japanese Patent Laid-Open No. 2003-96061

Patent Document 3: Japanese Patent Laid-Open No. 2000-229927

SUMMARY OF INVENTION

Technical Problem

Latent curing agents that constitute one-component epoxy resin compositions are required to achieve both favorable curability and storage stability after being mixed with epoxy resin, and further required to have favorable penetration into narrow gap sites of electronic members or between dense fibers such as carbon fibers or glass fibers. However, any latent curing agent that satisfies these characteristics has not yet been obtained.

For example, Patent Document 1 discloses, as a curing agent, a liquid bisimidazole compound obtained by modifying imidazole with acrylate. However, a problem thereof is that the curing agent is susceptible to improvement in storage stability.

Patent Document 2 discloses an aminimide compound obtained using 1-aminopyrrolidine. However, a problem thereof is that the compound is a solid and is therefore inferior in penetration at ordinary temperature.

Patent Document 3 discloses a liquid aminimide compound. However, a problem thereof is that the compound is not easy to handle because 1,1-dimethylhydrazine which is designated as an autoreactive substance and toxicity is used as a starting material.

Accordingly, in light of the problems of the conventional techniques mentioned above, an object of the present invention is to provide an aminimide compound that is excellent in penetration and has excellent curability and storage stability.

Solution to Problem

The present inventors have conducted diligent studies and consequently completed the present invention by finding that an aminimide compound having a specific structure is excellent in penetration, curability, and storage stability.

Specifically, the present invention is as follows.

[1] An aminimide compound represented by the following formula (1), (2) or (3):

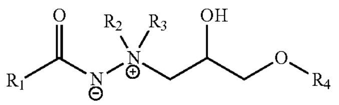
(1)

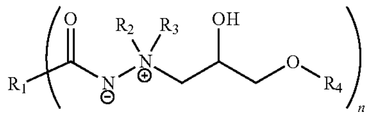
(2)

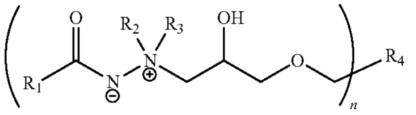
(3)

wherein each $R_1$ independently represents a hydrogen atom, or a monovalent or n-valent organic group having 1 to 15 carbon atoms and optionally having a hydroxy group, a carbonyl group, an ester bond, or an ether bond; $R_2$ and $R_3$ each independently represent an unsubstituted or substituted alkyl group having 1 to 12 carbon atoms, aryl group, aralkyl group, or heterocyclic ring having 7 or less carbon atoms in which $R_2$ and $R_3$ are linked to each other; each $R_4$ independently represents a hydrogen atom, or a monovalent or n-valent organic group having 1 to 30 carbon atoms and optionally containing an oxygen atom; and n represents an integer of 1 to 3.

[2] An aminimide compound according to [1], wherein the $R_1$ in the formula (1) or (3) is a group represented by the following formula (4) or (5):

(4)

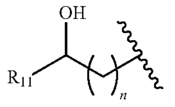

(5)

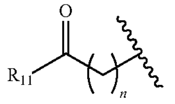

wherein each $R_{11}$ independently represents an alkyl group having 1 to 5 carbon atoms, an alkoxy group having 1 to 5 carbon atoms, an aryl group, or an aralkyl group having 7 to 9 carbon atoms, and each n independently represents an integer of 0 to 6.

[3] An aminimide compound according to [1], wherein the $R_1$ in the formula (2) is a group represented by the following formula (6) or (7):

(6)

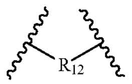

(7)

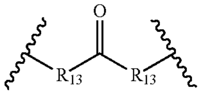

wherein $R_{12}$ and $R_{13}$ each independently represent a single bond, an alkyl group having 1 to 5 carbon atoms, an aryl group, or an aralkyl group having 7 to 9 carbon atoms.

[4] An aminimide compound according to any one of [1] to [3], wherein at least one of $R_2$ and $R_3$ represents an aralkyl group.

[5] An aminimide compound according to any one of [1] to [3], wherein the heterocyclic ring having 7 or less carbon atoms in which $R_2$ and $R_3$ are linked to each other is a heterocyclic ring formed by $R_{23}$ and $N^+$ in the formula (1), (2) or (3) and represented by the following formula (8):

(8)

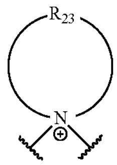

wherein $R_{23}$ represents a group that forms a heterocyclic structure together with $N^+$.

[6] An aminimide compound according to any one of [1] to [5], wherein the $R_4$ in the formula (1) or (2) is a linear or branched alkyl group having 3 to 12 carbon atoms, or a linear or branched alkenyl group having 3 to 6 carbon atoms.

[7] An aminimide compound according to any one of [1] to [5], wherein the $R_4$ in the formula (3) is a group represented by the following formula (9) or (10):

(9)

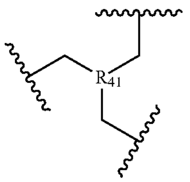

(10)

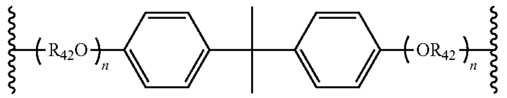

wherein $R_{41}$ and $R_{42}$ each independently represent an alkyl group having 1 to 5 carbon atoms, an aryl group, or an aralkyl group, and each n independently represents an integer of 0 to 10.

[8] An aminimide compound according to any one of [1] to [7], wherein the aminimide compound is represented by the formula (2) or (3) wherein n is 2 or 3.

[9] An aminimide compound according to any one of [1] to [7], wherein the aminimide compound is represented by the formula (2) or (3) wherein n is 2.

[10] An aminimide compound according to any one of [1] to [9], wherein a viscosity at 25° C. is 1300 Pa·s or less.

[11] An aminimide compound according to any one of [1] to [10], wherein a difference ($T_{peak}$-$T_{onset}$) between a peak top temperature ($T_{peak}$) and an onset temperature ($T_{onset}$) of an exothermic peak related to the decomposition of the N—N bond in differential thermal analysis is 45° C. or less.

[12] An aminimide composition containing a plurality of aminimide compounds according to any one of [1] to [11].

[13] An aminimide composition according to [12], containing aminimide compounds represented by the formula (1) and the formula (3).

[14] A curing agent containing an aminimide compound according to any one of [1] to [10], or an aminimide composition according to [12] or [13].

[15] An epoxy resin composition containing epoxy resin (α), and a curing agent (β) according to [14].

[16] The epoxy resin composition according to [15], wherein a content of the curing agent (β) is 1 to 50 parts by mass per 100 parts by mass of the epoxy resin (α).

[17] The epoxy resin composition according to [15] or [16], further containing an acid anhydride-based curing agent (γ).

[18] A method for producing an aminimide compound according to any one of [1] to [11], or an aminimide compound in an aminimide composition according to [12] or [13], containing a reaction step of reacting a carboxylic acid ester compound (A), a hydrazine compound (B), and a glycidyl ether compound (C).

[19] An encapsulant which is a cured product of an epoxy resin composition according to any one of [15] to [17].

[20] An adhesive containing an epoxy resin composition according to [15], wherein the curing agent (β) contains an aminimide compound represented by the formula (3).

Advantageous Effect of Invention

The present invention can provide a latent curing agent that is excellent in penetration and has excellent curability and storage stability.

DESCRIPTION OF EMBODIMENTS

Hereinafter, the mode for carrying out the present invention (hereinafter, simply referred to as the "present embodiment") will be described in detail. The present embodiment is given for illustrating the present invention and does not intend to limit the present invention to the contents described below. The present invention can be carried out by appropriately making changes or modifications without departing from the spirit of the present invention.

[Aminimide Compound]

The aminimide compound of the present embodiment is represented by the following formula (1), (2) or (3):

(1)

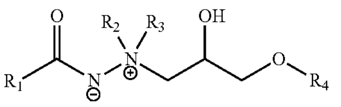

(2)

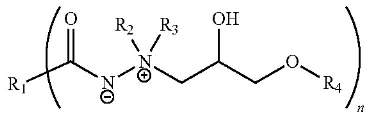

(3)

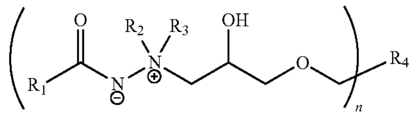

wherein each $R_1$ independently represents a hydrogen atom, or a monovalent or n-valent organic group having 1 to 15 carbon atoms and optionally having a hydroxy group, a carbonyl group, an ester bond, or an ether bond; $R_2$ and $R_3$ each independently represent an unsubstituted or substituted alkyl group having 1 to 12 carbon atoms, aryl group, aralkyl group, or heterocyclic ring having 7 or less carbon atoms in which $R_2$ and $R_3$ are linked to each other; each $R_4$ independently represents a hydrogen atom, or a monovalent or n-valent organic group having 1 to 30 carbon atoms and optionally containing an oxygen atom; and n represents an integer of 1 to 3.

The aminimide compound of the present embodiment does not contain any substituent having curing performance in the state of the aminimide compound, and therefore does not cause addition reaction with an epoxy group even if dissolved with the epoxy resin at room temperature. However, as shown in a reaction formula given below, the N—N bond is cleaved by heating to form acyl nitrene and tertiary amine. The acyl nitrene is converted to isocyanate through 1,2-transfer reaction. The isocyanate and the tertiary amine thus formed have curing performance and lead to curing by causing addition reaction with an epoxy group. Specifically, the aminimide compound of the present embodiment functions as a latent curing agent.

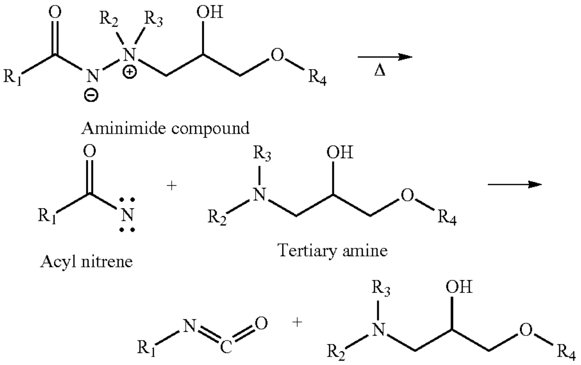

Aminimide compound

Acyl nitrene

Tertiary amine

Isocyanate

Tertiary amine

Since the aminimide compound of the present embodiment has a hydroxy group, as shown in a reaction formula given below, addition reaction occurs between the isocyanate and the tertiary amine formed by heating, which are in turn converted to a structure having tertiary amine and a urethane bond in one molecule. This structure has excellent curing performance owing to the isocyanate and the tertiary amine. Therefore, the aminimide compound of the present embodiment functions as a latent curing agent having excellent curing performance.

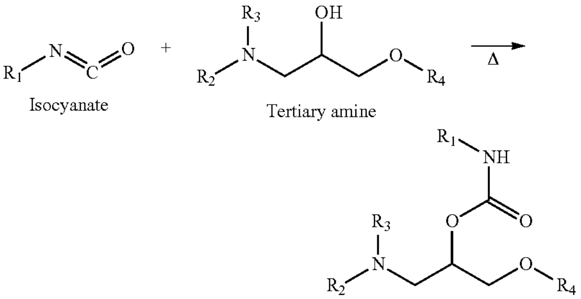

Isocyanate

Tertiary amine

Urethane bond-containing tertiary amine

The compound represented by the formula (2) is a compound in which compounds represented by the formula (1) are linked to each other through the n-valent bonding group $R_1$. The compound represented by the formula (3) is a compound in which compounds represented by the formula (1) are linked to each other through the n-valent bonding group $R_4$. The compound represented by the formula (2) forms a n-valent isocyanate compound and monovalent tertiary amine by heating. The compound represented by the formula (3) form a monovalent isocyanate compound and n-valent tertiary amine by heating.

The peak top temperature ($T_{peak}$) of the decomposition temperature of the N—N bond in the aminimide compound of the present embodiment is preferably 100° C. or higher and 250° C. or lower, more preferably 100° C. or higher and 220° C. or lower, further preferably 100° C. or higher and 200° C. or lower, still further preferably 100° C. or higher and 180° C. or lower.

When $T_{peak}$ is 100° C. or higher, storage stability tends to be more improved. When $T_{peak}$ is 250° C. or lower, the curing performance of the aminimide compound tends to be more improved. In this context, the peak top temperature ($T_{peak}$) of the decomposition temperature of the N—N bond is the peak top temperature of an exothermic peak related to the decomposition of the N—N bond, and refers to the highest temperature of the exothermic peak in differential thermal analysis.

The onset temperature ($T_{onset}$) of the decomposition temperature of the N—N bond in the aminimide compound of the present embodiment is preferably 80° C. or higher and 200° C. or lower, more preferably 80° C. or higher and 185° C. or lower, further preferably 80° C. or higher and 170° C. or lower, still further preferably 80° C. or higher and 160° C. or lower.

When $T_{onset}$ is 80° C. or higher, storage stability tends to be more improved. When $T_{onset}$ is 200° C. or lower, the curing performance of the aminimide compound tends to be more improved. In this context, the onset temperature ($T_{onset}$) of the decomposition temperature of the N—N bond refers to the onset temperature of the exothermic peak in differential thermal analysis. More specifically, the point of intersection between the tangent of the maximum slope of a rising portion of the exothermic peak and the extrapolation line of a baseline is regarded as the onset temperature ($T_{onset}$).

The difference ($T_{peak}-T_{onset}$) between the peak top temperature ($T_{peak}$) and the onset temperature ($T_{onset}$) is preferably 45° C. or less, more preferably 40° C. or less, further preferably 35° C. or less, still further preferably 30° C. or less. When the difference ($T_{peak}-T_{onset}$) is 45° C. or less, the decomposition of the N—N bond by heating progresses rapidly so that the steep response of curing reaction tends to be more improved. The lower limit of the difference ($T_{peak}-T_{onset}$) is not particularly limited and is preferably 5° C. or more, more preferably 10° C. or more, further preferably 15° C. or more.

The peak top temperature ($T_{peak}$), the onset temperature ($T_{onset}$), and the difference ($T_{peak}-T_{onset}$) can be controlled by adjusting functional groups of the aminimide compound of the present embodiment. For example, $R_1$ tends to contribute to lower energy of the cleavage of the N—N bond, and $R_2$ and $R_3$ tend to contribute to lower energy of cleavage reaction by destabilization ascribable to steric hindrance. Thus, these temperatures can be controlled by appropriately using a group that contributes to improvement in curing performance and other groups in combination as $R_1$, $R_2$ and $R_3$ mentioned later.

The aminimide compound of the present embodiment is preferably a liquid compound at ordinary temperature.

In the present embodiment, a viscosity at 25° C. can be used as an index that indicates being liquid at ordinary temperature. The viscosity at 25° C. of the aminimide compound of the present embodiment is preferably 1300 Pa·s or less, more preferably 900 Pa·s or less, further preferably 800 Pa·s or less, still further preferably 700 Pa·s or less.

The lower limit value of the viscosity at 25° C. is not particularly limited and is preferably 0.01 Pa·s or more.

When the aminimide compound of the present embodiment is a liquid compound at ordinary temperature, particularly, has a viscosity of 1300 Pa·s or less at 25° C., solubility or dispersibility in an epoxy resin composition and penetration into a base material or the like are more improved.

The viscosity of the aminimide compound of the present embodiment can be controlled within the numeric range described above by adjusting functional groups of $R_1$ to $R_4$ in the formula (1) to the formula (3).

In the formula (1), (2) or (3), it is considered that: $R_1$ contributes to lower energy of the cleavage of the N—N bond; $R_2$ and $R_3$ contribute to lower energy of cleavage reaction by destabilization ascribable to steric hindrance; and $R_4$ contributes to the liquefication of the compound and the suppression of decrease in the glass transition temperature of the resulting cured product, though the present invention is not particularly limited by this idea. Hereinafter, the details of each group will be described.

In the formulas (1), (2) and (3), each $R_1$ independently represents a hydrogen atom, or a monovalent or n-valent organic group having 1 to 15 carbon atoms and optionally having a hydroxy group, a carbonyl group, an ester bond, or an ether bond. Examples of such an organic group include, but are not particularly limited to, hydrocarbon groups, groups in which a hydrogen atom bonded to a carbon atom in a hydrocarbon group is replaced with a hydroxy group or a carbonyl group, and groups in which one or some carbon atoms constituting a hydrocarbon group are replaced with an ester bond or an ether bond. Examples of such a hydrocarbon group include: linear, branched, or cyclic alkyl groups such as a methyl group, an ethyl group, a propyl group, a butyl group, a pentyl group, a hexyl group, a heptyl group, an octyl group, and an ethylhexyl group; alkenyl groups such as a vinyl group, a propynyl group, a butynyl group, a pentynyl group, a hexynyl group, an octynyl group, a decynyl group, a dodecynyl group, a hexadecynyl group, and an octadecynyl group; aryl groups such as a phenyl group; and aralkyl groups composed of combinations of an alkyl group and a phenyl group, such as a methylphenyl group, an ethylphenyl group, and a propylphenyl group.

The organic group represented by $R_1$ may have an additional substituent. Examples of the substituent include, but are not particularly limited to, a halogen atom, an alkoxy group, a carbonyl group, a cyano group, an azo group, an azi group, a thiol group, a sulfo group, a nitro group, a hydroxy group, an acyl group, and an aldehyde group.

The number of carbon atoms in the organic group represented by $R_1$ is 1 to 15, preferably 1 to 12, more preferably 1 to 7. When the number of carbon atoms in the organic group represented by $R_1$ falls within the range described above, a liquid aminimide compound that fulfills the viscosity described above is easily obtained. Furthermore, the curing performance of the aminimide compound tends to be more improved. When the number of carbon atoms in the organic group represented by $R_1$ falls within the range described above, the ease of obtainment of a starting material is more improved.

Among those described above, $R_1$ in the formula (1) or (3) is preferably a group represented by the formula (4) or (5) given below. By having such a group, a liquid aminimide compound that fulfills the viscosity described above is easily obtained. Furthermore, the curing performance of the aminimide compound tends to be more improved.

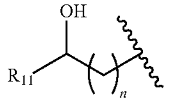
(4)

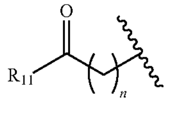
(5)

wherein each $R_{11}$ independently represents an alkyl group having 1 to 5 carbon atoms, an alkoxy group having 1 to 5 carbon atoms, an aryl group, or an aralkyl group having 7 to 9 carbon atoms, and each n independently represents an integer of 0 to 6.

Among those described above, a group of the formula (5) wherein n is 0 or 1 is preferred. The compound represented by the formula (1) or (3) thereby has a diketone structure in the $R_1$—C(═O)— structure. Such a diketone structure tends to more improve the curing performance of the aminimide compound.

The number of carbon atoms in $R_{11}$ and n in the formula (4) or (5) are adjusted such that the maximum value of the number of carbon atoms in the group represented by the formula (4) or (5) does not exceed 15.

$R_1$ in the formula (2) is preferably a group represented by the formula (6) or (7) given below. By having such a group, a liquid aminimide compound that fulfills the viscosity described above is easily obtained. Furthermore, the curing performance of the aminimide compound tends to be more improved.

(6)

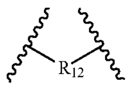

(7)

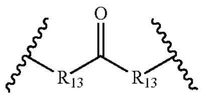

wherein $R_{12}$ and $R_{13}$ each independently represent a single bond, an alkyl group having 1 to 5 carbon atoms, an aryl group, or an aralkyl group having 7 to 9 carbon atoms.

Among those described above, $R_{13}$ in the formula (7) is preferably a single bond or a methyl group. The compound represented by the formula (2) thereby has a diketone structure in the $R_1$—C(═O)— structure. Such a diketone structure tends to more improve the curing performance of the aminimide compound.

In the formulas (1), (2) and (3), $R_2$ and $R_3$ each independently represent an unsubstituted or substituted alkyl group having 1 to 12 carbon atoms, aryl group, aralkyl group, or heterocyclic ring having 7 or less carbon atoms in which $R_2$ and $R_3$ are linked to each other.

Examples of the alkyl group having 1 to 12 carbon atoms represented by $R_2$ or $R_3$ include, but are not particularly limited to: linear alkyl groups such as a methyl group, an ethyl group, a propyl group, a n-butyl group, a n-pentyl group, a n-hexyl group, a n-octyl group, a n-decyl group, and a n-dodecyl group; branched alkyl groups such as an isopropyl group, an isobutyl group, a t-butyl group, a neopentyl group, a 2-hexyl group, a 2-octyl group, a 2-decyl group, and a 2-dodecyl group; and cyclic alkyl groups such as a cyclopropyl group, a cyclobutyl group, a cyclopentyl group, a cyclohexyl group, a cyclooctyl group, a cyclodecyl group, and a cyclododecyl group. The alkyl group may be a combination of a linear alkyl group or a branched alkyl group and a cyclic alkyl group. The alkyl group may further contain an unsaturated bonding group.

The number of carbon atoms in each alkyl group represented by $R_2$ or $R_3$ is independently 1 to 12, preferably 2 to 10, more preferably 5 to 10. A compound, such as dimethylhydrazine, which has a small number of carbon atoms in an alkyl group of asymmetric dialkylhydrazine, has a risk such as explosion as well as is toxic to human bodies. However, when the number of carbon atoms in the alkyl group represented by $R_2$ or $R_3$ is 2 or more, use of such a starting material having a risk such as toxicity can be avoided. When the number of carbon atoms in the alkyl group represented by $R_2$ or $R_3$ is 5 or more, a liquid aminimide compound that fulfills the viscosity described above is easily obtained. Furthermore, the curing performance of the aminimide compound tends to be more improved.

Examples of the aryl group represented by $R_2$ or $R_3$ include, but are not particularly limited to, a phenyl group and a naphthyl group. Examples of the aralkyl group represented by $R_2$ or $R_3$ include, but are not particularly limited to, a methylphenyl group, an ethylphenyl group, a methylnaphthyl group, and a dimethylnaphthyl group. Among them, at least one of $R_2$ and $R_3$ is preferably an aralkyl group, more preferably a methylphenyl group (benzyl group). The curing performance of the aminimide compound thereby tends to be more improved. The number of carbon atoms in the aryl group or the aralkyl group represented by $R_2$ or $R_3$ is not particularly limited and is preferably 6 to 20.

Examples of the substituent for the alkyl group, the aryl group, or the aralkyl group represented by $R_2$ or $R_3$ include, but are not particularly limited to, a halogen atom, an alkoxy group, a carbonyl group, a cyano group, an azo group, an azi group, a thiol group, a sulfo group, a nitro group, a hydroxy group, an acyl group, and an aldehyde group.

$R_2$ and $R_3$ may be linked to each other to constitute a heterocyclic ring having 7 or less carbon atoms. Examples of such a heterocyclic ring include, but are not particularly limited to, a heterocyclic ring formed by $R_{23}$ and $N^+$ in the formula (1), (2) or (3) and represented by the formula (8) given below. $R_{23}$ represents a group in which $R_2$ and $R_3$ are linked to each other.

(8)

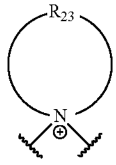

wherein $R_{23}$ represents a group that forms a heterocyclic structure together with $N^+$.

Examples of the heterocyclic ring formed by $R_{23}$ and $N^+$ include, but are not particularly limited to: 4-membered rings such as an azetidine ring; 5-membered rings such as a pyrrolidine ring, a pyrrole ring, a morpholine ring, and a thiazine ring; 6-membered rings such as a piperidine ring; and 7-membered rings such as a hexamethyleneimine ring and an azepine ring.

Among them, the heterocyclic ring is preferably a pyrrole ring, a morpholine ring, a thiazine ring, a piperidine ring, a hexamethyleneimine ring, or an azepine ring, more preferably a 6-membered ring or a 7-membered ring. By having such a group, a liquid aminimide compound that fulfills the viscosity described above is easily obtained. Furthermore, the curing performance of the aminimide compound tends to be more improved.

Examples of the substituent include, but are not particularly limited to, an alkyl group, an aryl group, and the substituent mentioned above for $R_2$ and $R_3$. When the heterocyclic ring has an alkyl group as a substituent, examples thereof can include a methyl group bonded to the carbon atom adjacent to $N^+$.

In the formulas (1), (2) and (3), $R_4$ represents a hydrogen atom, or a monovalent or n-valent organic group having 1 to 30 carbon atoms and optionally containing an oxygen atom. Examples of such an organic group include, but are not particularly limited to, hydrocarbon groups, groups in which a hydrogen atom bonded to a carbon atom in a hydrocarbon group is replaced with a hydroxy group, a carbonyl group, or a group containing a silicon atom, and groups in which one or some carbon atoms constituting a hydrocarbon group are replaced with an ester bond, an ether bond, or a silicon atom. Examples of such a hydrocarbon group include: linear, branched, or cyclic alkyl groups such as a methyl group, an ethyl group, a propyl group, a butyl group, a pentyl group, a hexyl group, a heptyl group, an octyl group, and an ethylhexyl group; alkenyl groups such as a vinyl group, a propynyl group, a butynyl group, a pentynyl group, a hexynyl group, an octynyl group, a decynyl group, a dodecynyl group, a hexadecynyl group, and an octadecynyl group; aryl groups such as a phenyl group; and aralkyl groups composed of combinations of an alkyl group and a phenyl group, such as a methylphenyl group, an ethylphenyl group, and a propylphenyl group.

Alternatively, the hydrocarbon group represented by $R_4$ contains a bisphenol skeleton such as a bisphenol A-type skeleton, a bisphenol AP-type skeleton, a bisphenol B-type skeleton, a bisphenol C-type skeleton, a bisphenol E-type skeleton, or a bisphenol F-type skeleton. Examples of the organic group containing the bisphenol skeleton include, but are not particularly limited to, groups in which a polyoxyalkylene group is added to a hydroxy group of each bisphenol skeleton.

Among them, the organic group represented by $R_4$ in the formula (1) or (2) is preferably an alkyl group, an alkenyl group, or an aralkyl group, more preferably an alkyl group or an alkenyl group, further preferably a branched alkyl group or a branched alkenyl group. These preferred groups may have a substituent. By having such a group, a liquid aminimide compound that fulfills the viscosity described above is easily obtained. Furthermore, the curing performance of the aminimide compound tends to be more improved. Moreover, Tg of a cured product obtained using the aminimide compound tends to be more improved.

The number of carbon atoms in the organic group represented by $R_4$ is 1 to 30 as mentioned above, preferably 1 to 20, more preferably 1 to 15, further preferably 1 to 8. When the number of carbon atoms in the organic group represented by $R_4$ falls within the range described above, a liquid aminimide compound that fulfills the viscosity described above is easily obtained. Furthermore, the curing performance of the aminimide compound tends to be more improved. Moreover, Tg of a cured product obtained using the aminimide compound is more improved. When the number of carbon atoms in the organic group represented by $R_4$ falls within the range described above, the ease of obtainment of a starting material is more improved.

Among those described above, $R_4$ in the formula (1) or (2) is preferably a linear or branched alkyl group having 3 to 12 carbon atoms, or a linear or branched alkenyl group having 3 to 6 carbon atoms. By having such a group, a liquid aminimide compound that fulfills the viscosity described above is easily obtained. Furthermore, the curing performance of the aminimide compound tends to be more improved.

$R_4$ in the formula (3) is preferably a group represented by the formula (9) or (10) given below. By having such a group, a liquid aminimide compound that fulfills the viscosity described above is easily obtained. Furthermore, the curing performance of the aminimide compound tends to be more improved.

(9)

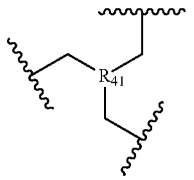

(10)

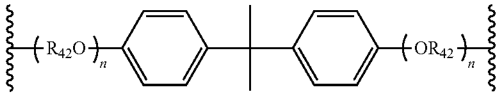

wherein $R_{41}$ and $R_{42}$ each independently represent an alkyl group having 1 to 5 carbon atoms, an aryl group, or an aralkyl group, and each n independently represents an integer of 0 to 10.

The aminimide compound of the present embodiment is preferably represented by the formula (2) or (3) wherein n is 2 or 3, more preferably 2. An effect of improving curability is thereby obtained.

[Aminimide Composition]

The aminimide composition of the present embodiment contains a plurality of aminimide compounds represented by the formula (1), (2) and/or (3). The aminimide composition contains a plurality of aminimide compounds of the present embodiment because an effect of improving characteristics is obtained, from the viewpoint of curing temperature control or viscosity control. The aminimide composition may contain a plurality of aminimide compounds that are represented by the same formula but differ in structure.

The aminimide composition preferably contains aminimide compounds represented by the formula (1) and the formula (3), particularly, from the viewpoint of viscosity control.

In the case of containing a plurality of aminimide compounds, the content ratio thereof is set to 0.1% by mass to 99.5% by mass of the aminimide compound represented by the formula (1). Viscosity control thereby tends to be easy.

The aminimide composition containing a plurality of aminimide compounds may be obtained by mixing the plurality of aminimide compounds, or can also be obtained by producing the plurality of aminimide compounds at the same time by a method for producing an aminimide compound mentioned later.

[Methods for Producing Aminimide Compound and Aminimide Composition]

The method for producing the aminimide compound of the present embodiment is not particularly limited as long as the method produces the aminimide compound having the structure described above.

The method for producing the aminimide composition of the present embodiment includes a method of mixing a plurality of aminimide compounds obtained by a method mentioned later, and a method of producing a plurality of aminimide compounds at the same time to obtain a mixture.

Examples of the method for producing the aminimide compound of the present embodiment include a method containing a reaction step of reacting a carboxylic acid ester compound (A), a hydrazine compound (B), and a glycidyl ether compound (C).

Hereinafter, the production method will be described.

Examples of the carboxylic acid ester compound (A) include, but are not particularly limited to, monocarboxylic acid ester compounds and dicarboxylic acid ester compounds.

Specific examples of the monocarboxylic acid ester compound include methyl lactate, ethyl lactate, methyl mandelate, methyl acetate, methyl propionate, methyl butyrate, methyl isobutyrate, methyl valerate, methyl isovalerate, methyl pivalate, methyl heptanoate, methyl octanoate, methyl acrylate, methyl methacrylate, methyl crotonate, methyl isocrotonate, methyl benzoylformate, 2-methoxybenzoylmethyl, 3-methoxybenzoylmethyl, 4-methoxybenzoylmethyl, 2-ethoxybenzoylmethyl, and 4-t-butoxybenzoylmethyl. Ethyl esters, propyl esters, and the like may be used instead of these compounds. Specific examples of the dicarboxylic acid ester compound include dimethyl oxalate, dimethyl malonate, dimethyl succinate, dimethyl tartrate, dimethyl glutarate, dimethyl adipate, dimethyl pimelate, dimethyl suberate, dimethyl azelate, dimethyl sebacate, dimethyl maleate, dimethyl fumarate, dimethyl itaconate, dimethyl phthalate, dimethyl isophthalate, dimethyl terephthalate, dimethyl 1,3-acetonedicarboxylate, and diethyl 1,3-acetonedicarboxylate. Diethyl esters, dipropyl esters, and the like may be used instead of these compounds.

Among them, ethyl lactate, methyl mandelate, methyl acetate, methyl propionate, methyl butyrate, methyl isobutyrate, methyl valerate, methyl isovalerate, methyl pivalate-methyl acrylate, methyl methacrylate, methyl crotonate, methyl isocrotonate, methyl benzoylformate, dimethyl oxalate, dimethyl malonate, dimethyl succinate, dimethyl tartrate, dimethyl glutarate, dimethyl adipate, dimethyl pimelate, dimethyl suberate, dimethyl azelate, dimethyl maleate, dimethyl fumarate, dimethyl phthalate, dimethyl isophthalate, dimethyl terephthalate, dimethyl 1,3-acetonedicarboxylate, and diethyl 1,3-acetonedicarboxylate are preferred from the viewpoint of curability and liquefication.

Among them, ethyl lactate, methyl mandelate, methyl benzoylformate, dimethyl oxalate, dimethyl malonate, dimethyl succinate, dimethyl glutarate, dimethyl adipate, and diethyl 1,3-acetonedicarboxylate are more preferred from the viewpoint of the ease of obtainment. These carboxylic acid ester compounds (A) may each be used singly or may be used in combination of two or more thereof.

Examples of the hydrazine compound (B) include, but are not particularly limited to, dimethylhydrazine, diethylhydrazine, methylethylhydrazine, methylpropylhydrazine, methylbutylhydrazine, methylpentylhydrazine, methylhexylhydrazine, ethylpropylhydrazine, ethylbutylhydrazine, ethylpentylhydrazine, ethylhexylhydrazine, dipropylhydrazine, dibutylhydrazine, dipentylhydrazine, dihexylhydrazine, methylphenylhydrazine, ethylphenylhydrazine, methyltolylhydrazine, ethyltolylhydrazine, diphenylhydrazine, benzylphenylhydrazine, dibenzylhydrazine, dinitrophenylhydrazine, 1-aminopiperidine, N-aminohomopiperidine, 1-amino-2,6-dimethylpiperidine, 1-aminopyrrolidine, 1-amino-2-methylpyrrolidine, 1-amino-2-phenylpyrrolidine, and 1-aminomorpholine.

Among them, dimethylhydrazine, dibenzylhydrazine, 1-aminopiperidine, 1-aminopyrrolidine, and 1-aminomorpholine are preferred from the viewpoint of curability and liquefication. Among them, dibenzylhydrazine and 1-aminopiperidine are more preferred from the viewpoint of the ease of obtainment and safety. These hydrazine compounds (B) may each be used singly or may be used in combination of two or more thereof.

The glycidyl ether compound (C) is not particularly limited, and, for example, a monofunctional monoglycidyl ether compound or a difunctional or higher polyglycidyl ether compound can be used. Specific examples of the monoglycidyl ether compound include methyl glycidyl ether, ethyl glycidyl ether, n-butyl glycidyl ether, t-butyl glycidyl ether, 2-ethylhexyl glycidyl ether, dodecyl glycidyl ether, higher alcohol glycidyl ether, allyl glycidyl ether, phenyl glycidyl ether, cresyl glycidyl ether, o-phenylphenol glycidyl ether, benzyl glycidyl ether, biphenylyl glycidyl ether, 4-t-butylphenyl glycidyl ether, t-butyldimethylsilyl glycidyl ether, and 3-[diethoxy(methyl)silyl]propyl glycidyl ether. Specific examples of the polyglycidyl ether compound include: aliphatic polyglycidyl ether such as ethylene glycol diglycidyl ether, diethylene glycol diglycidyl ether, triethylene glycol diglycidyl ether, polyethylene glycol diglycidyl ether, propylene glycol diglycidyl ether, dipropylene glycol diglycidyl ether, tripropylene glycol diglycidyl ether, polypropylene glycol diglycidyl ether, neopentyl glycol diglycidyl ether, butanediol glycidyl ether, hexanediol glycidyl ether, trimethylolpropane polyglycidyl ether, glycerin polyglycidyl ether, diglycerin polyglycidyl ether, polyglycerin polyglycidyl ether, and sorbitol polyglycidyl ether; alicyclic polyglycidyl ether compounds such as bisphenol A-type diglycidyl ether, bisphenol F-type diglycidyl ether, bisphenol S-type diglycidyl ether, ethylene oxide-added bisphenol A-type diglycidyl ether, propylene oxide-added bisphenol A-type diglycidyl ether, and hydrogenation products of their condensates; and aromatic polyglycidyl ether compounds such as resorcinol diglycidyl ether.

Among them, methyl glycidyl ether, ethyl glycidyl ether, n-butyl glycidyl ether, t-butyl glycidyl ether, 2-ethylhexyl glycidyl ether, allyl glycidyl ether, phenyl glycidyl ether, t-butyldimethylsilyl glycidyl ether, ethylene glycol diglycidyl ether, diethylene glycol diglycidyl ether, neopentyl glycol diglycidyl ether, butanediol glycidyl ether, hexanediol glycidyl ether, trimethylolpropane polyglycidyl ether, bisphenol A-type diglycidyl ether, bisphenol F-type diglycidyl ether, ethylene oxide-added bisphenol A-type diglycidyl ether, and propylene oxide-added bisphenol A-type diglycidyl ether are preferred from the viewpoint of curability and liquefication.

Among them, n-butyl glycidyl ether, t-butyl glycidyl ether, 2-ethylhexyl glycidyl ether, allyl glycidyl ether, trimethylolpropane polyglycidyl ether, ethylene oxide-added bisphenol A-type diglycidyl ether, butanediol glycidyl ether, hexanediol glycidyl ether, and propylene oxide-added bisphenol A-type diglycidyl ether are more preferred from the viewpoint of the ease of obtainment and Tg of a cured product. These glycidyl ether compounds (C) may each be used singly or may be used in combination of two or more thereof.

The amounts of the carboxylic acid ester compound (A), the hydrazine compound (B), and the glycidyl ether compound (C) added to the reaction system can be represented by the molar ratios of functional groups. The carboxylic acid ester group of the carboxylic acid ester compound (A) is preferably 0.8 to 3.0 mol, more preferably 0.9 to 2.8 mol, further preferably 0.95 to 2.5 mol, per mol of the primary amine of the hydrazine compound (B). The glycidyl group of the glycidyl ether compound (C) is preferably 0.8 to 2.0 mol, more preferably 0.9 to 1.5 mol, further preferably 0.95 to 1.4 mol, per mol of the primary amine of the hydrazine compound (B).

The aminimide composition containing aminimide compounds represented by the formula (1) and the formula (3) can be produced at the same time by controlling the amount of the glycidyl group of the glycidyl ether compound (C) added per mol of the primary amine of the hydrazine compound (B). Specifically, the glycidyl group of the glycidyl ether compound (C) is preferably 0.1 to 3.0 mol, more preferably 0.3 to 2.0 mol, further preferably 0.5 to 1.0 mol, per mol of the primary amine of the hydrazine compound (B).

In the methods for producing the aminimide compound and the aminimide composition of the present embodiment, the reaction of the components (A) to (C) progresses without the use of a solvent. It is preferred to use a solvent from the viewpoint that the reaction progresses homogeneously.

The solvent is not particularly limited as long as the solvent does not react with the components (A) to (C). Examples thereof include: alcohols such as methanol, ethanol, 1-propanol, 2-propanol, butanol, and t-butyl alcohol; and ethers such as tetrahydrofuran and diethyl ether.

The reaction temperature is preferably 10 to 70° C., more preferably 20 to 60° C. When the reaction temperature is 10° C. or higher, the progression of the reaction is accelerated and the purity of the resulting aminimide compound tends to be more improved. When the reaction temperature is 60° C. or lower, the purity of the aminimide compound tends to be more improved because the polymerization reaction between glycidyl ether compounds (C) can be efficiently suppressed.

The reaction time is preferably 1 to 7 days, more preferably 1 to 6 days, further preferably 1 to 4 days.

After the completion of reaction, the obtained reaction product can be purified by a purification method known in the art, such as washing, extraction, recrystallization, or column chromatography. For example, a reaction solution of the product dissolved in an organic solvent is washed with water. Then, an organic layer is heated under ordinary pressure or reduced pressure so that unreacted starting materials or the organic solvent can be removed from the reaction solution to recover an aminimide compound. The obtained reaction product can be further purified by column chromatography to recover an aminimide compound.

The solvent for use in washing is not particularly limited as long as the solvent can dissolve residues of starting materials. Hexane, pentane, and cyclohexane are preferred from the viewpoint of yield, purity, and the ease of removal.

The organic solvent for use in extraction is not particularly limited as long as the solvent can dissolve the aminimide compound of interest. Ethyl acetate, dichloromethane, chloroform, carbon tetrachloride, toluene, diethyl ether, and methyl isobutyl ketone are preferred, and ethyl acetate, chloroform, toluene, and methyl isobutyl ketone are more preferred, from the viewpoint of yield, purity, and the ease of removal.

A packing agent known in the art, such as alumina or silica gel, can be used in column chromatography. One or a mixture of developing solvents known in the art, such as ethyl acetate, dichloromethane, chloroform, carbon tetrachloride, tetrahydrofuran, diethyl ether, acetone, methyl isobutyl ketone, acetonitrile, methanol, ethanol, and isopropanol, can be used.

[Curing Agent]

The curing agent of the present embodiment contains the aminimide compound or the aminimide composition of the present embodiment mentioned above.

The curing agent of the present embodiment may contain an additional component other than the aminimide compound or the aminimide composition.

Examples of the additional component include other blending agents such as inorganic fillers, flame retardants, core-shell rubber particles, silane coupling agents, mold release agents, and pigments. In the case of containing an additional component other than the aminimide compound or the aminimide composition of the present embodiment, the content thereof is preferably 90% by mass or less.

The aminimide compound of the present embodiment is preferably in a liquid form at ordinary temperature. In such a case, the amide compound is excellent, particularly, in compatibility with epoxy resin, and can be suitably used as an epoxy resin composition supplemented with an additional component. Hereinafter, the epoxy resin composition will be described.

[Epoxy Resin Composition]

The epoxy resin composition of the present embodiment contains epoxy resin (α) and the curing agent (β) of the present embodiment mentioned above. The epoxy resin composition of the present embodiment may optionally further contain an additional curing agent other than the aminimide compound and the aminimide composition of the present embodiment mentioned above, or an arbitrary component generally known to be used in epoxy resin compositions of various applications.

Examples of the epoxy resin (α) include, but are not particularly limited to: difunctional epoxy resins such as bisphenol A-type epoxy resin, bisphenol F-type epoxy resin, bisphenol AD-type epoxy resin, bisphenol M-type epoxy resin, bisphenol P-type epoxy resin, tetrabromobisphenol A-type epoxy resin, biphenyl-type epoxy resin, tetramethylbiphenyl-type epoxy resin, tetrabromobiphenyl-type epoxy resin, diphenyl ether-type epoxy resin, benzophenone-type epoxy resin, phenyl benzoate-type epoxy resin, diphenyl sulfide-type epoxy resin, diphenyl sulfoxide-type epoxy resin, diphenyl sulfone-type epoxy resin, diphenyl disulfide-type epoxy resin, naphthalene-type epoxy resin, anthracene-type epoxy resin, hydroquinone-type epoxy resin, methylhydroquinone-type epoxy resin, dibutylhydroquinone-type epoxy resin, resorcinol-type epoxy resin, methylresorcinol-type epoxy resin, catechol-type epoxy resin, N,N-diglycidyl aniline-type epoxy resin, ethylene oxide-added bisphenol A-type epoxy resin, propylene oxide-added bisphenol A-type epoxy resin, ethylene oxide-added bisphenol F-type epoxy resin, and propylene oxide-added bisphenol F-type epoxy resin; trifunctional epoxy resins such as trisphenol-type epoxy resin, N,N-diglycidyl aminobenzene-type epoxy resin, o-(N,N-diglycidyl amino)toluene-type epoxy resin, triazine-type epoxy resin, ethylene oxide-added trisphenol-type epoxy resin, and propylene oxide-added trisphenol-type epoxy resin; tetrafunctional epoxy resins such as tetraglycidyl diaminodiphenylmethane-type epoxy resin and diaminobenzene-type epoxy resin; polyfunctional epoxy resins such as phenol novolac-type epoxy resin, cresol novolac-type epoxy resin, triphenylmethane-type epoxy resin, tetraphenylethane-type epoxy resin, dicyclopentadiene-type epoxy resin, naphthol aralkyl-type epoxy resin, and brominated phenol novolac-type epoxy resin; and alicyclic epoxy resins. These epoxy resins may each be used singly or may be used in combination of two or more thereof. Epoxy resin obtained by modifying any of these resins with isocyanate or the like can also be used in combination therewith.

In the epoxy resin composition of the present embodiment, the curing agent (β) mentioned above may be used in combination with an additional curing agent other than it. Examples of the additional curing agent include, but are not particularly limited to: amine-based curing agents such as imidazoles, diaminodiphenylmethane, diaminodiphenylsulfone, diethylenetriamine, triethylenetetramine, isophoronediamine, polyalkylene glycol polyamine, and polyamide resin synthesized from a linolenic acid dimer and ethylenediamine; amide-based curing agents such as dicyandiamide; acid anhydride-based curing agents such as phthalic anhydride, trimellitic anhydride, pyromellitic anhydride, maleic anhydride, tetrahydrophthalic anhydride, methyl tetrahydrophthalic anhydride, methyl nadic anhydride, hexahydrophthalic anhydride, and methyl hexahydrophthalic anhydride; phenol-based curing agents such as polyhydric phenol compounds and their modification products, such as phenol novolac resin, cresol novolac resin, phenol aralkyl resin, cresol aralkyl resin, naphthol aralkyl resin, biphenyl-modified phenol resin, biphenyl-modified phenol aralkyl resin, dicyclopentadiene-modified phenol resin, aminotriazine-modified phenol resin, naphthol novolac resin, naphthol-phenol co-condensed novolac resin, and naphthol-cresol co-condensed novolac resin; and $BF_3$-amine complexes and guanidine derivatives. These curing agents may each be used singly or may be used in combination of two or more thereof.

Among the additional curing agents other than the curing agent (β), it is preferred to further contain an acid anhydride-based curing agent (γ) with the emphasis on penetration.

In the epoxy resin composition of the present embodiment, the content of the curing agent (β) for use as a curing agent is preferably 1 to 50 parts by mass, more preferably 1 to 30 parts by mass, further preferably 2 to 20 parts by mass, per 100 parts by mass in total of the epoxy resin (α). When the content of the curing agent (β) falls within the range described above, more favorable physical properties of curing tend to be obtained while curing reaction sufficiently progresses.

In the case of using the curing agent (β) as a curing accelerator in the epoxy resin composition of the present embodiment configured to contain an additional curing agent other than the curing agent (β), the content of the curing agent (β) is preferably 0.1 to 30 parts by mass, more preferably 0.5 to 20 parts by mass, further preferably 1 to 15 parts by mass, per 100 parts by mass in total of the epoxy resin (α). When the content of the curing agent (β) as a curing accelerator falls within the range described above, more favorable physical properties of curing tend to be obtained while curing reaction sufficiently progresses, owing to the curing agent (β) that functions as a curing catalyst for the additional curing agent.

In the epoxy resin composition that employs the curing agent (β) containing the aminimide compound of the present embodiment as a curing accelerator and employs the acid anhydride-based curing agent (γ) mentioned above as a curing agent, the equivalent ratio of the acid anhydride group of the acid anhydride-based curing agent (γ) to the epoxy group of the epoxy resin (α) (acid anhydride group/epoxy group) is preferably 0.80 to 1.20, more preferably 0.85 to 1.15, further preferably 0.90 to 1.10.

When the amounts of the epoxy resin (α) and the acid anhydride-based curing agent (γ) used fall within the range described above, more favorable physical properties of curing tend to be obtained while curing reaction sufficiently progresses.

The epoxy resin composition of the present embodiment may optionally further contain an inorganic filler. Examples of the inorganic filler include, but are not particularly limited to, fused silica, crystalline silica, alumina, talc, silicon nitride, and aluminum nitride.

In the epoxy resin composition of the present embodiment, the content of the inorganic filler is not particularly limited as long as the content falls within a range that produces the effects of the present embodiment. In the epoxy resin composition of the present embodiment, the content of the inorganic filler is usually preferably 90% by mass or less. When the content of the inorganic filler falls within the range described above, the epoxy resin composition tends to have a sufficiently low viscosity and be excellent in handleability.

The epoxy resin composition of the present embodiment may optionally further contain an additional blending agent such as a flame retardant, a silane coupling agent, a mold release agent, or a pigment. A suitable one can be appropriately selected as such an additional blending agent as long as the effects of the present embodiment are obtained. Examples of the flame retardant include, but are not particularly limited to, halides, phosphorus atom-containing compounds, nitrogen atom-containing compounds, and inorganic flame retardant compounds.

[Cured Product]

A cured product is obtained by curing the epoxy resin composition of the present embodiment. The cured product of the epoxy resin composition of the present embodiment is obtained, for example, by thermally curing the epoxy resin composition by a conventional method known in the art. For example, first, the epoxy resin and the curing agent described above, and further, an optional curing accelerator, inorganic filler, and/or blending agent, etc. are sufficiently mixed until homogeneous using an extruder, a kneader, a roll, or the like to obtain an epoxy resin composition. Then, the epoxy resin composition can be molded by casting or using a transfer molding machine, a compression molding machine, an injection molding machine, or the like, and further heated under conditions of approximately 80 to 200° C. and approximately 2 to 10 hours to obtain a cured product.

Alternatively, the cured product can be obtained by, for example, the following method: first, the epoxy resin composition of the present embodiment is dissolved in a solvent such as toluene, xylene, acetone, methyl ethyl ketone, or methyl isobutyl ketone to obtain a solution. A base material such as glass fibers, carbon fibers, polyester fibers, polyamide fibers, alumina fibers, or paper is impregnated with the obtained solution, and dried by heating to obtain a prepreg. Next, the obtained prepreg can be molded by heat press to obtain a cured product.

[Application]

The epoxy resin composition of the present embodiment and the cured product thereof can be used in various applications in which epoxy resin is used as a material. The epoxy resin composition and the cured product are particularly useful in applications such as encapsulants, encapsulants for semiconductors, adhesives, print substrate materials, coating materials, and composite materials.

Among them, the epoxy resin composition and the cured product are suitably used in semiconductor encapsulants such as underfills and moldings, conductive adhesives such as anisotropically conductive films (ACFs), printed circuit boards such as solder resists and coverlay films, and composite materials such as prepregs prepared by impregnating glass fibers, carbon fibers, or the like with the epoxy resin composition.

(Adhesive)

The adhesive of the present embodiment contains the epoxy resin composition of the present embodiment mentioned above, and the curing agent (β) preferably contains an aminimide compound represented by the formula (3). An effect of improving penetration is thereby obtained.

(Electronic Member)

The cured product of the epoxy resin composition of the present embodiment can be used in various electronic members. Examples thereof include, but are not limited to, semiconductor encapsulants such as underfills and moldings, conductive adhesives such as ACF, printed circuit boards such as solder resists and coverlay films, and composite materials such as prepregs prepared by the impregnation of glass fibers, carbon fibers, or the like.

EXAMPLES

Next, the present invention will be described still more specifically with reference to Synthesis Examples, Comparative Synthesis Examples, Examples, and Comparative Examples. However, the present invention is not limited by these examples by any means.

In the description below, the terms "parts" and "%" are based on mass unless otherwise specified.

In Synthesis Examples mentioned later, aminimide compounds and aminimide compositions were synthesized. A viscosity at 25° C., a melting point, and an infrared absorption spectrum were each measured as the physical properties of the aminimide compounds and the aminimide compositions.

[Method for Measuring Viscosity at 25° C.]

The viscosity (Pa·s) at 25° C. of an aminimide compound was measured by adding dropwise the aminimide compound or an aminimide composition (approximately 0.3 mL) to a measurement cup and performing measurement using a type E viscometer ("TVE-35H" manufactured by Toki Sangyo Co., Ltd.) 15 minutes after the sample temperature reached 25° C.

In Table 1, "Nature" represents the state at 25° C.

[Method for Measuring Melting Point]

The melting point was measured as to only a sample that was a solid at ordinary temperature (25° C.). The melting point of an aminimide compound or an aminimide composition was defined as the peak top temperature of an endothermic peak under conditions given below.

Apparatus: Simultaneous thermogravimetry/differential thermal analysis apparatus ("TG/DTA7220" manufactured by Hitachi High-Tech Corp.)
Sample mass: Approximately 10 mg
Sample container: Open aluminum pan
Measurement temperature: 40° C. to 240° C.
Temperature increase rate: 5° C./min
Atmospheric gas: nitrogen
Gas flow rate: 40 mL/min

[Method for Measuring N—N Bond Decomposition Temperature]

The N—N bond decomposition peak top temperature of an aminimide compound or an aminimide composition was defined as the peak top temperature ($T_{peak}$) of an exothermic peak under measurement conditions given below. The N—N bond decomposition start temperature thereof was defined as the onset temperature ($T_{onset}$) of the exothermic peak. The onset temperature ($T_{onset}$) was determined from the point of intersection between the tangent of the maximum slope of a rising portion of the exothermic peak and the extrapolation line of a baseline. ($T_{peak}-T_{onset}$) was calculated therefrom.

<Measurement Conditions>

Apparatus: Simultaneous thermogravimetry/differential thermal analysis apparatus ("TG/DTA7220" manufactured by Hitachi High-Tech Corp.)
Sample mass: Approximately 10 mg
Sample container: Open aluminum pan
Measurement temperature: 40° C. to 240° C.
Temperature increase rate: 5° C./min
Atmospheric gas: nitrogen
Gas flow rate: 40 mL/min

[Method for Measuring Infrared Absorption Spectrum]

The infrared absorption spectrum was measured using a Fourier transform infrared spectrophotometer ("FT/IR-410" manufactured by JASCO Corp.). A method for preparing a measurement sample employed a liquid membrane method when the sample is liquid, and employed a tablet method when the sample is a solid.

The liquid membrane method is a method of sandwiching a sample between rock salt plates permeable to infrared ray to prepare a measurement sample in a film form.

The tablet method is a method of uniformly dispersing a sample in a potassium bromide powder using a mortar or the like, followed by pressing to prepare a measurement sample in a tablet form.

The presence or absence of an aminimide group-derived specific infrared absorption spectrum found at 1570 $cm^{-1}$ to 1620 $cm^{-1}$ was confirmed.

[Mass Spectrometric Measurement Method]

The mass spectrometric measurement was performed using QDa detector manufactured by Waters Corp. as a mass spectrometry (MS) detector.

A measurement sample was adjusted to a concentration of approximately 0.25% by mass using acetonitrile.

Solution sending conditions started at 90:10=methanol: water as an initial value, followed by 50:50=methanol:water 3 minutes later. Since a peak was observed at approximately 0.1 to 0.5 minutes, the peak was analyzed.

The mass spectrometry conditions of the QDa detector manufactured by Waters Corp. involved Mass (m/z) ES+ or 50-1250, a capillary voltage of 0.8 V, a cone voltage of 25 V, and a probe temperature of 600° C.

Each compound was observed at $H^+$-added monovalent m/z.

A 5 mM solution of ammonium acetate in methanol was sent at 0.45 mL/min to promote ionization.

In the description below, aminimide compounds and aminimide compositions were prepared.

The following Synthesis Examples are specific examples of the aminimide compound and the aminimide composition according to the present invention.

Synthesis Example 1

17.68 g (0.12 mol) of dimethyl succinate, 12.02 g (0.12 mol) of 1-aminopiperidine, 22.54 g (0.12 mol) of 2-ethylhexyl glycidyl ether, and 26.12 g (0.35 mol) of t-butyl alcohol were mixed to obtain a solution. This solution was reacted with stirring at 55° C. for 4 days to obtain a reaction solution. The obtained reaction solution was concentrated under reduced pressure at 55° C. so that t-butyl alcohol, secondarily produced alcohols, and unreacted starting materials were distilled off to obtain a liquid product. This product was dissolved in ethyl acetate, and unreacted starting material residues were removed by repetitive washing with water using a separating funnel to obtain an organic layer. This organic layer was concentrated under reduced pressure at 55° C. again to obtain 44.37 g (yield: 92.3%) of pale yellow liquid aminimide compound A (compound A). A measurement value of IR (neat): 1573 $cm^{-1}$ was obtained by the method for measuring an infrared absorption spectrum. A peak of m/z=401.5 was observed in mass spectrometry. It was thereby found that aminimide compound A represented by the following formula was obtained.

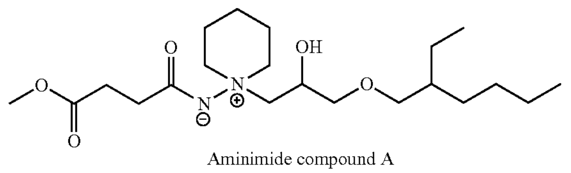 [SMILES: CCCCC(CC)COCC(O)C[N+]1([N-]C(=O)CCC(=O)OC)CCCCC1]

Aminimide compound A

Synthesis Example 2

17.68 g (0.12 mol) of dimethyl succinate, 12.02 g (0.12 mol) of 1-aminopiperidine, 12.09 g (0.04 mol) of trimethylolpropane polyglycidyl ether, and 20.90 g (0.28 mol) of t-butyl alcohol were mixed to obtain a solution. This solution was reacted with stirring at 55° C. for 3 days to obtain a reaction solution. The obtained reaction solution was concentrated under reduced pressure at 55° C. so that t-butyl alcohol, secondarily produced alcohols, and unreacted starting materials were distilled off to obtain a liquid product. This product was dissolved in ethyl acetate, and unreacted starting material residues were removed by repetitive washing with water using a separating funnel to obtain an organic layer. This organic layer was concentrated under reduced pressure at 55° C. again to obtain 33.46 g (yield: 88.5%) of pale yellow viscous aminimide compound B (compound B). A measurement value of IR (neat): 1576 $cm^{-1}$ was obtained by the method for measuring an infrared absorption spectrum. A peak of m/z=946.8 was observed in mass spectrometry. It was thereby found that aminimide compound B represented by the following formula was obtained.

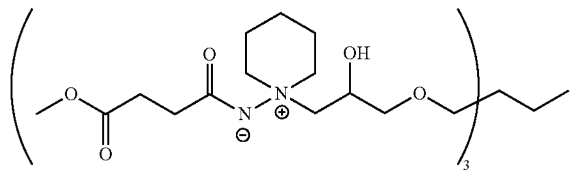

Aminimide compound B

Synthesis Example 3

19.70 g (0.12 mol) of methyl benzoylformate, 12.02 g (0.12 mol) of 1-aminopiperidine, 22.54 g (0.12 mol) of 2-ethylhexyl glycidyl ether, and 27.13 g (0.37 mol) of t-butyl alcohol were mixed to obtain a solution. This solution was reacted with stirring at 55° C. for 4 days to obtain a reaction solution. The obtained reaction solution was concentrated under reduced pressure at 55° C. so that t-butyl alcohol, secondarily produced alcohols, and unreacted starting materials were distilled off to obtain a liquid product. This product was dissolved in ethyl acetate, and unreacted starting material residues were removed by repetitive washing with water using a separating funnel to obtain an organic layer. This organic layer was concentrated under reduced pressure at 55° C. again to obtain 47.67 g (yield: 94.9%) of light brown liquid aminimide compound C (compound C). A measurement value of IR (neat): 1595 $cm^{-1}$ was obtained by the method for measuring an infrared absorption spectrum. A peak of m/z=419.5 was observed in mass spectrometry. It was thereby found that aminimide compound C represented by the following formula was obtained.

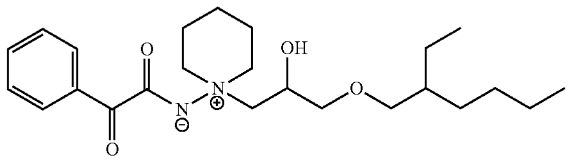

Aminimide compound C

Synthesis Example 4

24.27 g (0.12 mol) of diethyl 1,3-acetonedicarboxylate, 12.02 g (0.12 mol) of 1-aminopiperidine, 22.54 g (0.12 mol) of 2-ethylhexyl glycidyl ether, and 29.42 g (0.40 mol) of t-butyl alcohol were mixed to obtain a solution. This solution was reacted with stirring at 55° C. for 4 days to obtain a reaction solution. The obtained reaction solution was concentrated under reduced pressure at 55° C. so that t-butyl alcohol, secondarily produced alcohols, and unreacted starting materials were distilled off to obtain a liquid product. This product was dissolved in ethyl acetate, and unreacted starting material residues were removed by repetitive washing with water using a separating funnel to obtain an organic layer. This organic layer was concentrated under reduced pressure at 55° C. again to obtain 44.93 g (yield: 84.6%) of dark brown liquid aminimide compound D (compound D). A measurement value of IR (neat): 1609 $cm^{-1}$ was obtained by the method for measuring an infrared absorption spectrum. A peak of m/z=443.4 was observed in mass spectrometry. It was thereby found that aminimide compound D represented by the following formula was obtained.

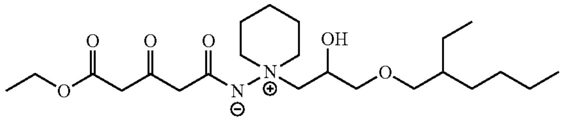

Aminimide compound D

Synthesis Example 5

12.13 g (0.06 mol) of diethyl 1,3-acetonedicarboxylate, 12.02 g (0.12 mol) of 1-aminopiperidine, 22.54 g (0.12 mol) of 2-ethylhexyl glycidyl ether, and 23.35 g (0.32 mol) of t-butyl alcohol were mixed to obtain a solution. This solution was reacted with stirring at 55° C. for 3 days to obtain a reaction solution. The obtained reaction solution was concentrated under reduced pressure at 55° C. so that t-butyl alcohol, secondarily produced alcohols, and unreacted starting materials were distilled off to obtain a liquid product. This product was dissolved in ethyl acetate, and unreacted starting material residues were removed by repetitive washing with water using a separating funnel to obtain an organic layer. This organic layer was concentrated under reduced pressure at 55° C. again to obtain 33.40 g (yield: 81.5%) of dark brown liquid aminimide compound E (compound E). A measurement value of IR (neat): 1586 $cm^{-1}$ was obtained by the method for measuring an infrared absorption spectrum. A peak of m/z=683.9 was observed in mass spectrometry. It was thereby found that aminimide compound E represented by the following formula was obtained.

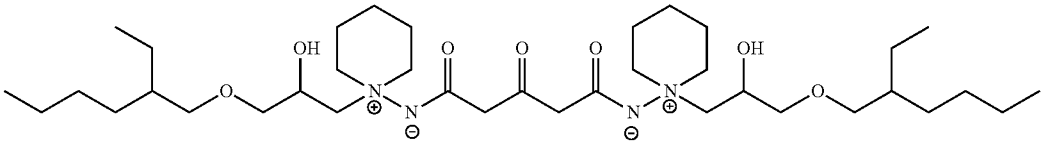

Aminimide compound E

Synthesis Example 6

14.17 g (0.12 mol) of dimethyl oxalate, 12.02 g (0.12 mol) of 1-aminopiperidine, 22.54 g (0.12 mol) of 2-ethylhexyl glycidyl ether, and 24.37 g (0.33 mol) of t-butyl alcohol were mixed to obtain a solution. This solution was reacted with stirring at 55° C. for 3 days to obtain a reaction solution. The obtained reaction solution was concentrated under reduced pressure at 55° C. so that t-butyl alcohol, secondarily produced alcohols, and unreacted starting materials were distilled off to obtain a liquid product. This product was dissolved in ethyl acetate, and unreacted starting material residues were removed by repetitive washing with water using a separating funnel to obtain an organic layer. This organic layer was concentrated under reduced pressure at 55° C. again to obtain 42.51 g (yield: 95.1%) of pale yellow liquid aminimide compound F (compound F). A measurement value of IR (neat): 1612 $cm^{-1}$ was obtained by the method for measuring an infrared absorption spectrum. A peak of m/z=372.5 was observed in mass spectrometry. It was thereby found that aminimide compound F represented by the following formula was obtained.

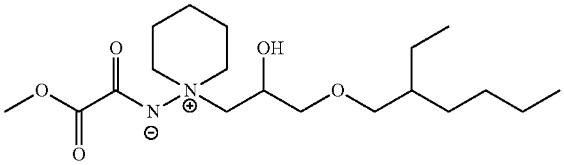

Aminimide compound F

Synthesis Example 7

7.09 g (0.06 mol) of dimethyl oxalate, 12.02 g (0.12 mol) of 1-aminopiperidine, 22.54 g (0.12 mol) of 2-ethylhexyl glycidyl ether, and 20.83 g (0.28 mol) of t-butyl alcohol were mixed to obtain a solution. This solution was reacted with stirring at 55° C. for 4 days to obtain a reaction solution. The obtained reaction solution was concentrated under reduced pressure at 55° C. so that t-butyl alcohol, secondarily produced alcohols, and unreacted starting materials were distilled off to obtain a liquid product. This product was dissolved in ethyl acetate, and unreacted starting material residues were removed by repetitive washing with water using a separating funnel to obtain an organic layer. This organic layer was concentrated under reduced pressure at 55° C. again to obtain 33.70 g (yield: 89.6%) of pale yellow viscous aminimide compound G (compound G). A measurement value of IR (neat): 1617 $cm^{-1}$ was obtained by the method for measuring an infrared absorption spectrum. A peak of m/z=627.8 was observed in mass spectrometry. It was thereby found that aminimide compound G represented by the following formula was obtained.

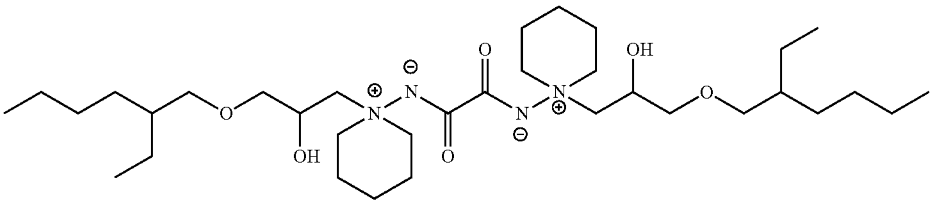

Aminimide compound G

Synthesis Example 8

19.70 g (0.12 mol) of methyl benzoylformate, 12.02 g (0.12 mol) of 1-aminopiperidine, 13.70 g (0.12 mol) of allyl glycidyl ether, and 22.71 g (0.31 mol) of t-butyl alcohol were mixed to obtain a solution. This solution was reacted with stirring at 55° C. for 4 days to obtain a reaction solution. The obtained reaction solution was concentrated under reduced pressure at 55° C. so that t-butyl alcohol, secondarily produced alcohols, and unreacted starting materials were distilled off to obtain a liquid product. This product was dissolved in ethyl acetate, and unreacted starting material residues were removed by repetitive washing with water using a separating funnel to obtain an organic layer. This organic layer was concentrated under reduced pressure at 55° C. again to obtain 37.54 g (yield: 90.3%) of brown liquid aminimide compound H (compound H). A measurement value of IR (neat): 1588 $cm^{-1}$ was obtained by the method for measuring an infrared absorption spectrum. A peak of m/z=347.4 was observed in mass spectrometry. It was thereby found that aminimide compound H represented by the following formula was obtained.

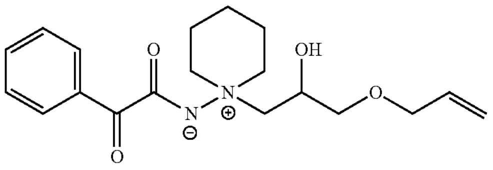

Aminimide compound H

Synthesis Example 9

7.46 g (0.045 mol) of methyl benzoylformate, 5.01 g (0.05 mol) of 1-aminopiperidine, 5.06 g (0.025 mol) of 1,4-butanediol diglycidyl ether, and 5.5 g (0.12 mol) of ethanol were mixed to obtain a solution. This solution was reacted with stirring at 55° C. for 1 day to obtain a reaction solution. The obtained reaction solution was concentrated under reduced pressure at 55° C. so that ethanol, secondarily produced alcohols, and unreacted starting materials were distilled off to obtain a liquid product. This product was dissolved in ethyl acetate, and unreacted starting material residues were removed by repetitive washing with water using a separating funnel to obtain an organic layer. This organic layer was concentrated under reduced pressure at 55° C. again to obtain 16.21 g (yield: 89.5%) of yellow liquid aminimide compound L (compound L). A measurement value of IR (neat): 1595 $cm^{-1}$ was obtained by the method for measuring an infrared absorption spectrum. A peak of m/z=667.6 was observed in mass spectrometry. It was thereby found that aminimide compound L represented by the following formula was obtained.

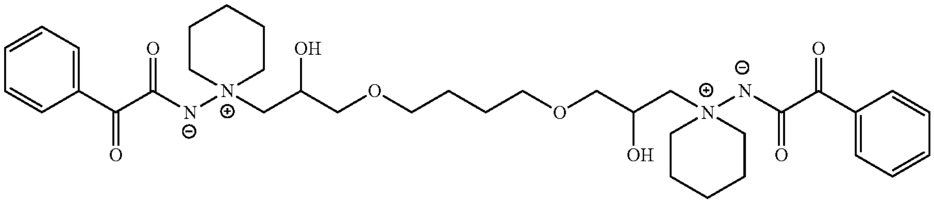

Aminimide compound L

Synthesis Example 10

7.46 g (0.045 mol) of methyl benzoylformate, 5.14 g (0.05 mol) of 1-aminopiperidine, 5.76 g (0.025 mol) of 1,6-hexanediol diglycidyl ether, and 5.5 g (0.12 mol) of ethanol were mixed to obtain a solution. This solution was reacted with stirring at 55° C. for 1 day to obtain a reaction solution. The obtained reaction solution was concentrated under reduced pressure at 55° C. so that ethanol, secondarily produced alcohols, and unreacted starting materials were distilled off to obtain a liquid product. Unreacted starting material residues were removed from this product by repetitive washing with hexane to obtain an organic layer. This organic layer was concentrated under reduced pressure at 55° C. again to obtain 17.07 g (yield: 88.1%) of red-brown liquid aminimide compound M (compound M). A measurement value of IR (neat): 1596 $cm^{-1}$ was obtained by the method for measuring an infrared absorption spectrum. A peak of m/z=695.6 was observed in mass spectrometry. It was thereby found that aminimide compound M represented by the following formula was obtained.

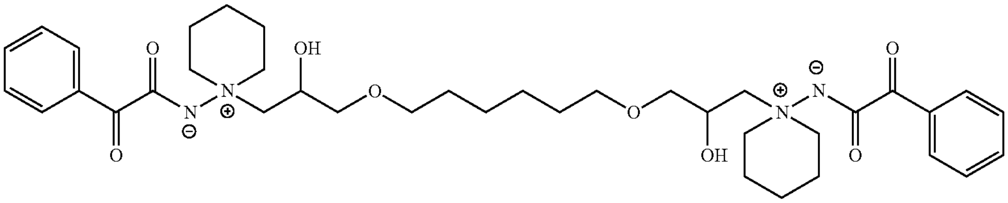

Aminimide compound M

Synthesis Example 11

7.86 g (0.065 mol) of ethyl lactate, 7.01 g (0.07 mol) of 1-aminopiperidine, 13.04 g (0.07 mol) of 2-ethylhexyl glycidyl ether, and 7.7 g (0.17 mol) of ethanol were mixed to obtain a solution. This solution was reacted with stirring at 55° C. for 1 day to obtain a reaction solution. The obtained reaction solution was concentrated under reduced pressure at 55° C. so that ethanol, secondarily produced alcohols, and unreacted starting materials were distilled off to obtain a liquid product. Unreacted starting material residues were removed from this product by repetitive washing with hexane to obtain an organic layer. This organic layer was concentrated under reduced pressure at 55° C. again to obtain 19.55 g (yield: 83.9%) of pale yellow liquid aminimide compound N (compound N). A measurement value of IR (neat): 1592 $cm^{-1}$ was obtained by the method for measuring an infrared absorption spectrum. A peak of m/z=359.5 was observed in mass spectrometry. It was thereby found that aminimide compound N represented by the following formula was obtained.

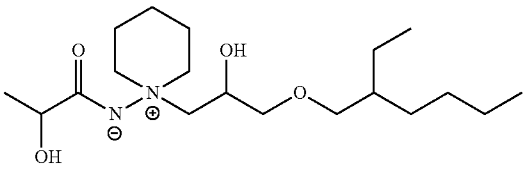

Aminimide compound N

Synthesis Example 12

4.68 g (0.040 mol) of ethyl lactate, 4.41 g (0.044 mol) of 1-aminopiperidine, 5.06 g (0.022 mol) of 1,6-hexanediol diglycidyl ether, and 5.5 g (0.12 mol) of ethanol were mixed to obtain a solution. This solution was reacted with stirring at 55° C. for 2 days to obtain a reaction solution. The obtained reaction solution was concentrated under reduced pressure at 55° C. so that ethanol, secondarily produced alcohols, and unreacted starting materials were distilled off to obtain a liquid product. Unreacted starting material residues were removed from this product by repetitive washing with hexane to obtain an organic layer. This organic layer was concentrated under reduced pressure at 55° C. again to obtain 12.22 g (yield: 85.7%) of pale yellow liquid aminimide compound O (compound O). A measurement value of IR (neat): 1592 $cm^{-1}$ was obtained by the method for measuring an infrared absorption spectrum. A peak of m/z=574.8 was observed in mass spectrometry. It was thereby found that aminimide compound O represented by the following formula was obtained.

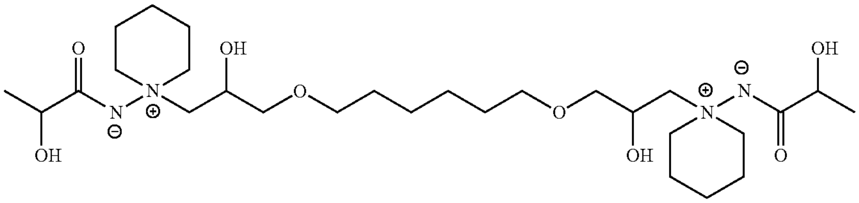

Aminimide compound O

Synthesis Example 13

3.54 g (0.030 mol) of ethyl lactate, 3.01 g (0.030 mol) of 1-aminopiperidine, 6.91 g (0.030 mol) of 1,6-hexanediol diglycidyl ether, and 8.0 g (0.17 mol) of ethanol were mixed to obtain a solution. This solution was reacted with stirring at 55° C. for 2 days to obtain a reaction solution. Unreacted starting material residues were removed from this product by repetitive washing with hexane to obtain an organic layer. This organic layer was concentrated under reduced pressure at 55° C. again to obtain 12.01 g of yellow liquid aminimide composition O2 (compound O2) which was a mixture of two aminimide compounds represented by formulas given below. A measurement value of IR (neat): 1593 $cm^{-1}$ was obtained by the method for measuring an infrared absorption spectrum. Peaks of m/z=575.6 and 421.4 were observed in mass spectrometry. The compound of m/z=575.6 is structurally similar to the aminimide compound O, and the compound of m/z=421.4 has a structure with a diol end on one side. It was thereby found that aminimide composition O2 represented by the following formulas was obtained.

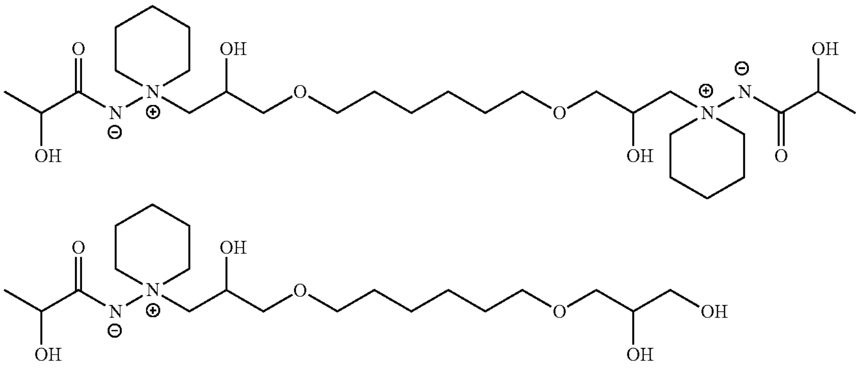

Aminimide composition O2

Synthesis Example 14

5.32 g (0.045 mol) of ethyl lactate, 4.51 g (0.045 mol) of 1-aminopiperidine, 6.91 g (0.030 mol) of 1,6-hexanediol diglycidyl ether, and 8.0 g (0.17 mol) of ethanol were mixed to obtain a solution. This solution was reacted with stirring at 55° C. for 2 days to obtain a reaction solution. Unreacted starting material residues were removed from this product by repetitive washing with hexane to obtain an organic layer. This organic layer was concentrated under reduced pressure at 55° C. again to obtain 14.56 g of yellow liquid aminimide composition O3 (compound O3) which was a mixture of two aminimide compounds represented by formulas given below. A measurement value of IR (neat): 1592 $cm^{-1}$ was obtained by the method for measuring an infrared absorption spectrum. Peaks of m/z=575.6 and 421.4 were observed in mass spectrometry. The compound of m/z=575.6 is structurally similar to the aminimide compound O, and the compound of m/z=421.4 has a structure with a diol end on one side. It was thereby found that aminimide composition O3 represented by the following formulas was obtained.

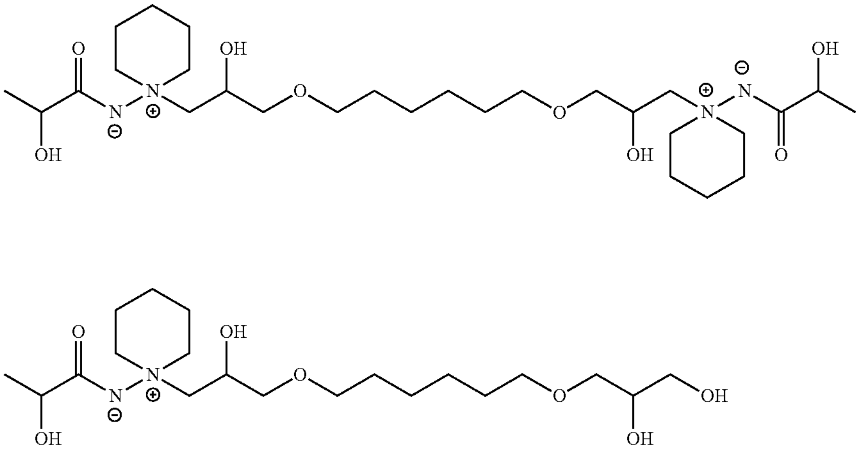

Aminimide composition O3

Synthesis Example 15

3.64 g (0.022 mol) of D,L-methyl mandelate, 2.34 g (0.023 mol) of 1-aminopiperidine, 4.35 g (0.023 mol) of 2-ethylhexyl glycidyl ether, and 3.0 g (0.07 mol) of ethanol were mixed to obtain a solution. This solution was reacted with stirring at 55° C. for 1 day to obtain a reaction solution. The obtained reaction solution was concentrated under reduced pressure at 55° C. so that ethanol, secondarily produced alcohols, and unreacted starting materials were distilled off to obtain a liquid product. Unreacted starting material residues were removed from this product by repetitive washing with hexane to obtain an organic layer. This organic layer was concentrated under reduced pressure at 55° C. again to obtain 8.41 g (yield: 90.5%) of pale yellow liquid aminimide compound P (compound P). A measurement value of IR (neat): 1603 $cm^{-1}$ was obtained by the method for measuring an infrared absorption spectrum. A peak of m/z=421.5 was observed in mass spectrometry. It was thereby found that aminimide compound P represented by the following formula was obtained.

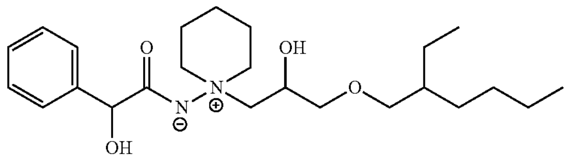

Aminimide compound P

Synthesis Example 16

9.97 g (0.060 mol) of D,L-methyl mandelate, 6.01 g (0.06 mol) of 1-aminopiperidine, 6.91 g (0.03 mol) of 1,6-hexanediol diglycidyl ether, and 8.0 g (0.17 mol) of ethanol were mixed to obtain a solution. This solution was reacted with stirring at 55° C. for 2 days to obtain a reaction solution. Unreacted starting material residues were removed from this product by repetitive washing with hexane to obtain an organic layer. This organic layer was concentrated under reduced pressure at 55° C. again to obtain 22.76 g (yield: 87.3%) of pale yellow liquid aminimide compound Q (compound Q). A measurement value of IR (neat): 1603 $cm^{-1}$ was obtained by the method for measuring an infrared absorption spectrum. A peak of m/z=699.7 was observed in mass spectrometry. It was thereby found that aminimide compound Q represented by the following formula was obtained.

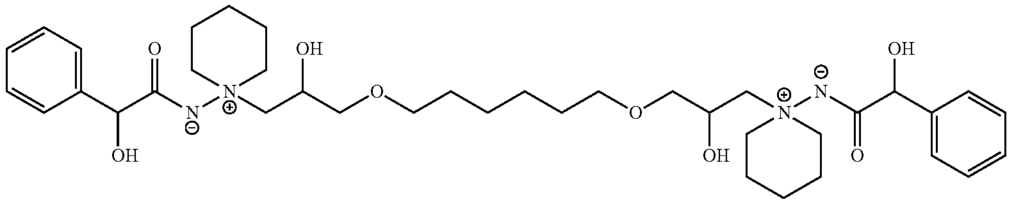

Aminimide compound Q

Synthesis Example 17

2.52 g (0.015 mol) of D,L-methyl mandelate, 1.5 g (0.015 mol) of 1-aminopiperidine, 2.30 g (0.01 mol) of 1,6-hexanediol diglycidyl ether, and 3.0 g (0.7 mol) of ethanol were mixed to obtain a solution. This solution was reacted with stirring at 55° C. for 1 day to obtain a reaction solution. Unreacted starting material residues were removed from this product by repetitive washing with hexane to obtain an organic layer. This organic layer was concentrated under reduced pressure at 55° C. again to obtain 4.91 g of pale yellow liquid aminimide composition Q2 (compound Q2) which was a mixture of two aminimide compounds represented by formulas given below. A measurement value of IR (neat): 1600 $cm^{-1}$ was obtained by the method for measuring an infrared absorption spectrum. Peaks of m/z=699.7 and 483.4 were observed in mass spectrometry. The compound of m/z=699.7 is structurally similar to the aminimide compound Q, and the compound of m/z=483.4 has a structure with a diol end on one side. It was thereby found that aminimide composition Q2 represented by the following formulas was obtained.

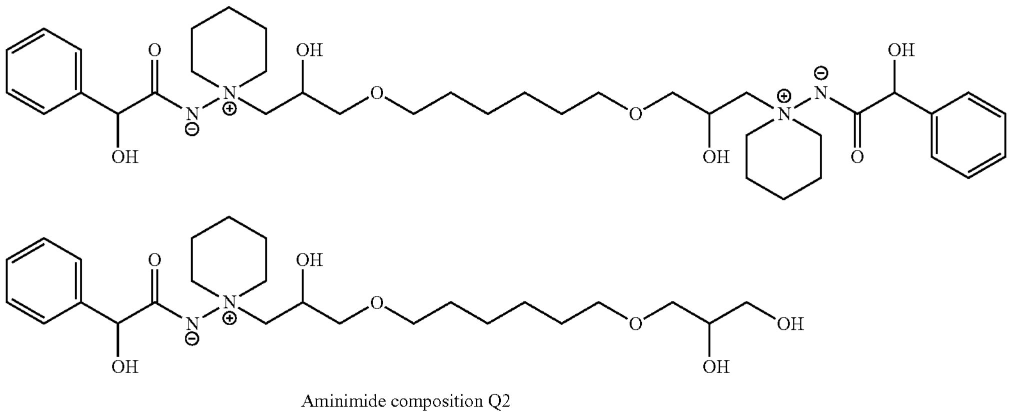

Aminimide composition Q2

Synthesis Example 18

2.92 g (0.02 mol) of dimethyl succinate, 2.01 g (0.02 mol) of 1-aminopiperidine, 3.73 g (0.02 mol) of 2-ethylhexyl glycidyl ether, and 4.0 g (0.09 mol) of ethanol were mixed to obtain a solution. This solution was reacted with stirring at 55° C. for 1 day to obtain a reaction solution. The obtained reaction solution was concentrated under reduced pressure at 55° C. so that ethanol, secondarily produced alcohols, and unreacted starting materials were distilled off to obtain a liquid product. Unreacted starting material residues were removed from this product by repetitive washing with hexane to obtain an organic layer. This organic layer was concentrated under reduced pressure at 55° C. again to obtain 4.87 g (yield: 60.7%) of pale yellow liquid aminimide compound R (compound R). A measurement value of IR (neat): 1578 $cm^{-1}$ was obtained by the method for measuring an infrared absorption spectrum. A peak of m/z=401.5 was observed in mass spectrometry. It was thereby found that aminimide compound R represented by the following formula was obtained.

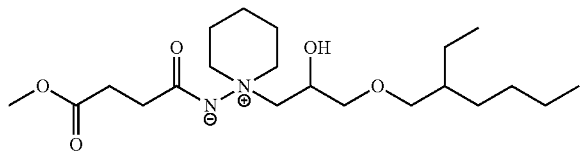

Aminimide compound R

Synthesis Example 19

4.38 g (0.03 mol) of dimethyl succinate, 3.00 g (0.03 mol) of 1-aminopiperidine, 3.45 g (0.015 mol) of 1,6-hexanediol diglycidyl ether, and 4.0 g (0.09 mol) of ethanol were mixed to obtain a solution. This solution was reacted with stirring at 55° C. for 1 day to obtain a product. Unreacted starting material residues were removed from this product by repetitive washing with hexane to obtain an organic layer. This organic layer was concentrated under reduced pressure at 55° C. again to obtain 10.06 g (yield: 81.3%) of pale yellow liquid aminimide compound S (compound S). A measurement value of IR (neat): 1578 $cm^{-1}$ was obtained by the method for measuring an infrared absorption spectrum. A peak of m/z=659.7 was observed in mass spectrometry. It was thereby found that aminimide compound S represented by the following formula was obtained.

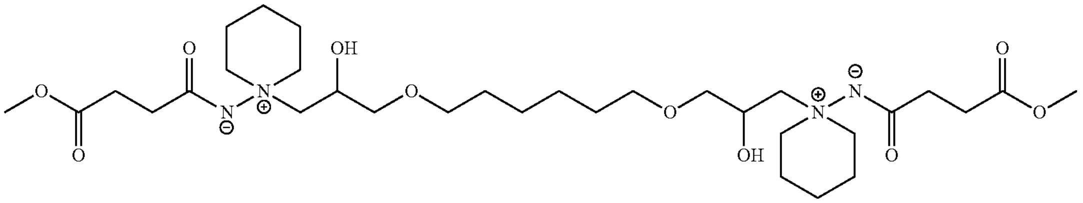

Aminimide compound S

Synthesis Example 20

3.28 g (0.023 mol) of dimethyl succinate, 2.25 g (0.023 mol) of 1-aminopiperidine, 3.45 g (0.015 mol) of 1,6-hexanediol diglycidyl ether, and 4.0 g (0.09 mol) of ethanol were mixed to obtain a solution. This solution was reacted with stirring at 55° C. for 1 day to obtain a product. Unreacted starting material residues were removed from this product by repetitive washing with hexane to obtain an organic layer. This organic layer was concentrated under reduced pressure at 55° C. again to obtain 8.31 g of pale yellow liquid aminimide composition S2 (compound S2) which was a mixture of two aminimide compounds represented by formulas given below. A measurement value of IR (neat): 1578 $cm^{-1}$ was obtained by the method for measuring an infrared absorption spectrum. Peaks of m/z=659.6 and 477.5 were observed in mass spectrometry. The compound of m/z=659.6 is structurally similar to the aminimide compound O, and the compound of m/z=477.5 has a structure with a diol end on one side. It was thereby found that aminimide composition S2 represented by the following formulas was obtained.

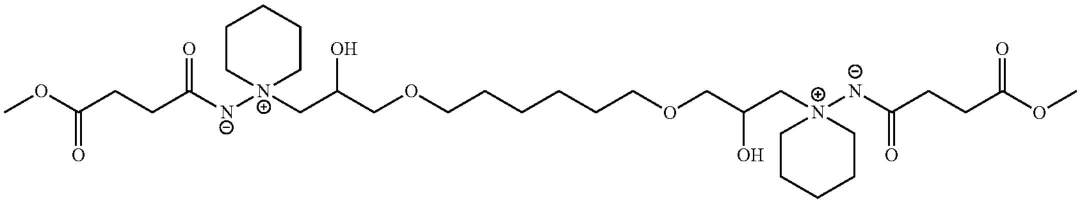

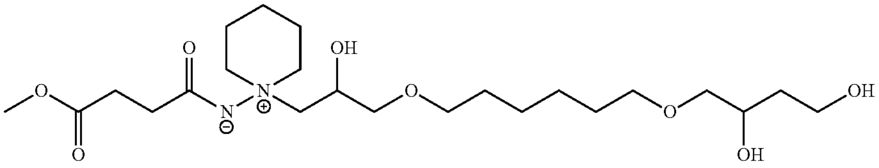

Aminimide composition S2

Synthesis Example 21

2.93 g (0.020 mol) of dimethyl succinate, 2.00 g (0.020 mol) of 1-aminopiperidine, 4.61 g (0.020 mol) of 1,6-hexanediol diglycidyl ether, and 4.0 g (0.09 mol) of ethanol were mixed to obtain a solution. This solution was reacted with stirring at 55° C. for 1 day to obtain a product. Unreacted starting material residues were removed from this product by repetitive washing with hexane to obtain an organic layer. This organic layer was concentrated under reduced pressure at 55° C. again to obtain 7.31 g of pale yellow liquid aminimide composition S3 (compound S3) which was a mixture of two aminimide compounds represented by formulas given below. A measurement value of IR (neat): 1578 $cm^{-1}$ was obtained by the method for measuring an infrared absorption spectrum. Peaks of m/z=659.6 and 477.5 were observed in mass spectrometry. The compound of m/z=659.6 is structurally similar to the aminimide compound O, and the compound of m/z=477.5 has a structure with a diol end on one side. It was thereby found that aminimide composition S3 represented by the following formulas was obtained.

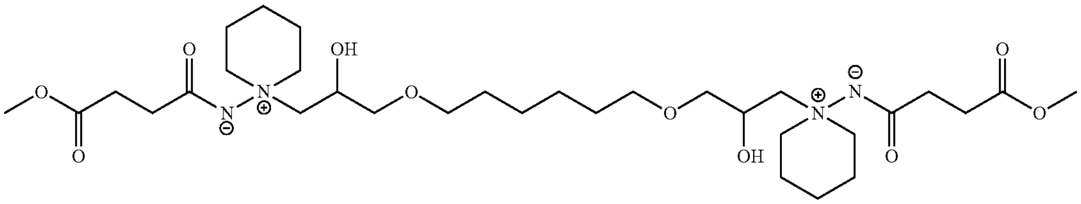

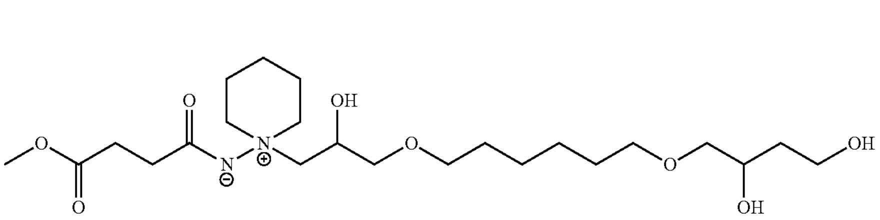

Aminimide composition S3

Synthesis Example 22

14.18 g (0.12 mol) of ethyl lactate, 12.02 g (0.12 mol) of 1-aminopiperidine, 13.70 g (0.12 mol) of allyl glycidyl ether, and 19.95 g (0.27 mol) of t-butyl alcohol were mixed to obtain a solution. This solution was reacted with stirring at 55° C. for 3 days to obtain a reaction solution. The obtained reaction solution was concentrated under reduced pressure at 55° C. so that t-butyl alcohol, secondarily produced alcohols, and unreacted starting materials were distilled off to obtain a solid product. This product was dissolved in ethyl acetate, and unreacted starting material residues were removed by repetitive washing with water using a separating funnel to obtain an organic layer. This organic layer was concentrated under reduced pressure at 55° C. again to obtain 29.14 g (yield: 84.8%) of pale yellow crystalline solid aminimide compound I (compound I). A measurement value of IR (KBr): 1592 $cm^{-1}$ was obtained by the method for measuring an infrared absorption spectrum. A peak of m/z=287.4 was observed in mass spectrometry. It was thereby found that aminimide compound I represented by the following formula was obtained.

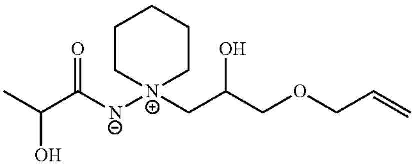

Aminimide compound I

Synthesis Example 23

19.94 g (0.12 mol) of DL-methyl mandelate, 12.02 g (0.12 mol) of 1-aminopiperidine, 13.70 g (0.12 mol) of allyl glycidyl ether, and 22.83 g (0.31 mol) of t-butyl alcohol were mixed to obtain a solution. This solution was reacted with stirring at 55° C. for 4 days to obtain a reaction solution. The obtained reaction solution was concentrated under reduced pressure at 55° C. so that t-butyl alcohol, secondarily produced alcohols, and unreacted starting materials were distilled off to obtain a solid product. This product was recrystallized using ethyl acetate to obtain 30.11 g (yield: 72.0%) of white crystalline solid aminimide compound J (compound J). A measurement value of IR (KBr): 1594 $cm^{-1}$ was obtained by the method for measuring an infrared absorption spectrum. A peak of m/z=349.3 was observed in mass spectrometry. It was thereby found that aminimide compound J represented by the following formula was obtained.

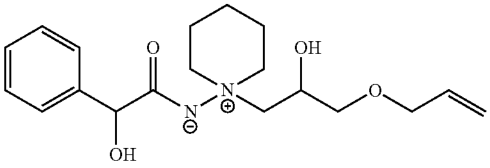

Aminimide compound J

Synthesis Example 24

8.77 g (0.06 mol) of dimethyl succinate, 12.02 g (0.12 mol) of 1-aminopiperidine, 22.54 g (0.12 mol) of 2-ethylhexyl glycidyl ether, and 21.67 g (0.29 mol) of t-butyl alcohol were mixed to obtain a solution. This solution was reacted with stirring at 55° C. for 4 days to obtain a reaction solution. The obtained reaction solution was concentrated under reduced pressure at 55° C. so that t-butyl alcohol, secondarily produced alcohols, and unreacted starting materials were distilled off to obtain a solid product. This product was dissolved in ethyl acetate, and unreacted starting material residues were removed by repetitive washing with water using a separating funnel. This organic layer was concentrated under reduced pressure at 55° C. again to obtain 33.05 g (yield: 84.1%) of white non-crystalline solid aminimide compound K (compound K). A measurement value of IR (KBr): 1570 $cm^{-1}$ was obtained by the method for measuring an infrared absorption spectrum. A peak of m/z=655.8 was observed in mass spectrometry. It was thereby found that aminimide compound K represented by the following formula was obtained.

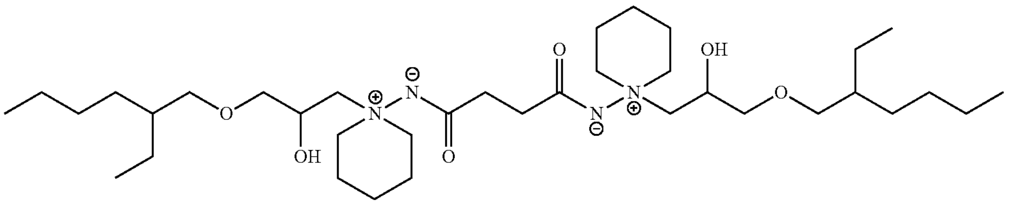

Aminimide compound K

Comparative Synthesis Example 1

13.22 g (0.12 mol) of 2-ethyl-4-methylimidazole and 22.11 g (0.12 mol) of 2-ethylhexyl acrylate were mixed to obtain a solution. This solution was reacted with stirring at 120° C. for 4 hours to obtain a liquid product. This product was dissolved in ethyl acetate, and unreacted starting materials were removed by repetitive washing with water using a separating funnel to obtain an organic layer. This organic layer was concentrated under reduced pressure at 55° C. again to obtain 33.46 g (yield: 33.46%) of a yellow liquid acrylate-imidazole adduct represented by a formula given below. A peak of m/z=294.4 was observed in mass spectrometry.

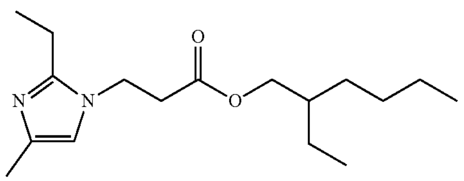

Acrylate-imidazole adduct

Evaluation results of Synthesis Examples 1 to 24 and Comparative Synthesis Example 1 are shown in Table 1 below.

TABLE 1

| Synthesis Example | Compound | Nature | Viscosity (@25° C.) Pa · s | Melting point ° C. | N—N bond decomposition temperature: Peak top temperature ($T_{peak}$) ° C. | N—N bond decomposition temperature: Start temperature ($T_{onset}$) ° C. | $T_{peak}$ − $T_{onset}$ ° C. |
|---|---|---|---|---|---|---|---|
| Synthesis Example 1 | Aminimide compound A | Liquid | 4.0 | — | 205.0 | 177.2 | 27.8 |
| Synthesis Example 2 | Aminimide compound B | Liquid | 844.0 | — | 211.7 | 184.5 | 27.2 |
| Synthesis Example 3 | Aminimide compound C | Liquid | 10.3 | — | 119.0 | 97.3 | 21.7 |
| Synthesis Example 4 | Aminimide compound D | Liquid | 0.2 | — | 181.5 | 146.0 | 35.5 |
| Synthesis Example 5 | Aminimide compound E | Liquid | 29.6 | — | 176.0 | 139.9 | 36.1 |
| Synthesis Example 6 | Aminimide compound F | Liquid | 0.8 | — | 179.3 | 150.7 | 28.6 |
| Synthesis Example 7 | Aminimide compound G | Liquid | 62.9 | — | 147.1 | 121.9 | 25.2 |
| Synthesis Example 8 | Aminimide compound H | Liquid | 83.0 | — | 123.3 | 100.6 | 22.7 |
| Synthesis Example 9 | Aminimide compound L | Liquid | 207.1 | — | 127.3 | 109.2 | 18.1 |
| Synthesis Example 10 | Aminimide compound M | Liquid | 132.2 | — | 128.3 | 107.8 | 20.5 |
| Synthesis Example 11 | Aminimide compound N | Liquid | 3.1 | — | 162.9 | 136.7 | 26.2 |
| Synthesis Example 12 | Aminimide compound O | Liquid | 306.4 | — | 168.4 | 131.6 | 36.8 |
| Synthesis Example 13 | Aminimide composition O2 | Liquid | 17.4 | — | 166.9 | 134.7 | 32.2 |
| Synthesis Example 14 | Aminimide composition O3 | Liquid | 205.3 | — | 166.5 | 138.4 | 28.1 |
| Synthesis Example 15 | Aminimide compound P | Liquid | 18.1 | — | 159.7 | 123.5 | 36.2 |
| Synthesis Example 16 | Aminimide compound Q | Liquid | 1180.0 | — | 163.5 | 132.1 | 31.4 |
| Synthesis Example 17 | Aminimide composition Q2 | Liquid | 219.6 | — | 162.7 | 130.1 | 32.6 |
| Synthesis Example 18 | Aminimide compound R | Liquid | 11.3 | — | 205.9 | 158.3 | 47.6 |
| Synthesis Example 19 | Aminimide compound S | Liquid | 46.9 | — | 211.7 | 171.7 | 40.0 |
| Synthesis Example 20 | Aminimide composition S2 | Liquid | 79.1 | — | 210.1 | 172.5 | 37.6 |
| Synthesis Example 21 | Aminimide composition S3 | Liquid | 12.0 | — | 209.4 | 173.1 | 36.3 |
| Synthesis Example 22 | Aminimide compound I | Solid | — | 68.7 | 160.5 | 134.9 | 25.6 |
| Synthesis Example 23 | Aminimide compound J | Solid | — | 110.3 | 158.0 | 141.2 | 16.8 |
| Synthesis Example 24 | Aminimide compound K | Solid | — | 75.6 | 182.3 | 154.9 | 27.4 |
| Comparative Synthesis Example 1 | Acrylate-imidazole adduct | Liquid | 0.1 | — | — | — | — |

Next, epoxy resin compositions containing the aminimide compounds and the aminimide compositions of [Synthesis Examples 1 to 24] and the acrylate-imidazole adduct of [Comparative Synthesis Example 1] as curing agents were prepared.

Curability and storage stability at room temperature (25° C.) were each measured as characteristics of the epoxy resin compositions.

[Preparation (1) of Epoxy Resin Composition]

In each of the epoxy resin compositions prepared in Examples and Comparative Examples given below, the following epoxy resin was used as a starting material.

Epoxy resin: Chang Chun Plastics Co., Ltd "BE-186EL"

For mixing starting materials, each aminimide compound, each aminimide composition, or the acrylate-imidazole adduct was added at 2 to 20 parts by mass per 100 parts by mass of the epoxy resin. The epoxy resin and the aminimide compound, the aminimide composition, or the acrylate-imidazole adduct were placed in a plastic stirring container and mixed by stirring using a rotation/revolution mixer ("ARE-310" manufactured by Thinky Corp.) to prepare an epoxy resin composition.

[Method (1) for Evaluating Curability]

In the method (1) for evaluating curability, 10 mg of the prepared epoxy resin composition was weighed into an aluminum container of a differential scanning calorimeter ("DSC220C" manufactured by Seiko Instruments Inc. (SII)), heated for 3 hours in an oven of 200° C., and then quenched. A reaction rate was calculated from change in DSC calorific value between before and after heating, and curability was evaluated from this reaction rate.

The curability was determined as follows: "◎" when the reaction rate was 95% or more; "○" when the reaction rate was less than 95% and 90% or more; "Δ" when the reaction rate was less than 90% and 80% or more; and "X" when the reaction rate was less than 80%.

[Method (1) for Evaluating Storage Stability]

In the method (1) for evaluating storage stability, the viscosity at 25° C. of the epoxy resin composition immediately after preparation was defined as "η1", and the viscosity at 25° C. of the epoxy resin composition preserved for 3 days in a thermostat bath of 25° C. was defined as "η2". A value calculated according to η2/η1 was determined as a viscosity increase ratio, and storage stability at room temperature was evaluated from this viscosity increase ratio.

The storage stability was determined as follows: "◎" when the viscosity increase ratio was less than 1.5-fold; "○" when the viscosity increase ratio was 1.5-fold or more and less than 2.0-fold; "Δ" when the viscosity increase ratio was 2.0-fold or more and less than 3.0-fold; and "X" when the viscosity increase ratio was 3.0-fold or more.

Example 1

20 g of the epoxy resin ("BE-186EL" manufactured by Chang Chun Plastics Co., Ltd) and 1.6 g of the aminimide compound A were placed in a plastic stirring container and mixed by stirring using a rotation/revolution mixer ("ARE-310" manufactured by Thinky Corp.) to prepare an epoxy resin composition. The curability was evaluated by the method (1) for evaluating curability, and the storage stability at room temperature was evaluated by the method (1) for evaluating storage stability.

Example 2

An epoxy resin composition was prepared and evaluated for its curability and storage stability at room temperature in the same manner as in Example 1 except that the amount of the aminimide compound A added was changed to 6.0 g.

Example 3

An epoxy resin composition was prepared and evaluated for its curability and storage stability at room temperature in the same manner as in Example 1 except that: the aminimide compound A was changed to the aminimide compound B; and the amount of the aminimide compound B added was changed to 2.0 g.

Example 4

An epoxy resin composition was prepared and evaluated for its curability and storage stability at room temperature in the same manner as in Example 1 except that: the aminimide compound A was changed to the aminimide compound C; and the amount of the aminimide compound C added was changed to 6.0 g.

Example 5

An epoxy resin composition was prepared and evaluated for its curability and storage stability at room temperature in the same manner as in Example 1 except that: the aminimide compound A was changed to the aminimide compound C; and the amount of the aminimide compound C added was changed to 0.4 g.

Example 6

An epoxy resin composition was prepared and evaluated for its curability and storage stability at room temperature in the same manner as in Example 1 except that the aminimide compound A was changed to the aminimide compound C.

Example 7

An epoxy resin composition was prepared and evaluated for its curability and storage stability at room temperature in the same manner as in Example 1 except that the aminimide compound A was changed to the aminimide compound D.

Example 8

An epoxy resin composition was prepared and evaluated for its curability and storage stability at room temperature in the same manner as in Example 1 except that the aminimide compound A was changed to the aminimide compound E.

Example 9

An epoxy resin composition was prepared and evaluated for its curability and storage stability at room temperature in the same manner as in Example 1 except that the aminimide compound A was changed to the aminimide compound F.

Example 10

An epoxy resin composition was prepared and evaluated for its curability and storage stability at room temperature in the same manner as in Example 1 except that the aminimide compound A was changed to the aminimide compound G.

Example 11

An epoxy resin composition was prepared and evaluated for its curability and storage stability at room temperature in the same manner as in Example 5 except that the aminimide compound C was changed to the aminimide compound H.

Example 12

An epoxy resin composition was prepared and evaluated for its curability and storage stability at room temperature in the same manner as in Example 1 except that the aminimide compound A was changed to the aminimide compound H.

Example 13

An epoxy resin composition was prepared and evaluated for its curability and storage stability at room temperature in the same manner as in Example 1 except that the aminimide compound A was changed to the aminimide compound L.

Example 14

An epoxy resin composition was prepared and evaluated for its curability and storage stability at room temperature in the same manner as in Example 1 except that the aminimide compound A was changed to the aminimide compound M.

Example 15

An epoxy resin composition was prepared and evaluated for its curability and storage stability at room temperature in the same manner as in Example 1 except that the aminimide compound A was changed to the aminimide compound N.

Example 16

An epoxy resin composition was prepared and evaluated for its curability and storage stability at room temperature in the same manner as in Example 2 except that the aminimide compound A was changed to the aminimide compound N.

Example 17

An epoxy resin composition was prepared and evaluated for its curability and storage stability at room temperature in the same manner as in Example 1 except that the aminimide compound A was changed to the aminimide compound O.

Example 18

An epoxy resin composition was prepared and evaluated for its curability and storage stability at room temperature in the same manner as in Example 2 except that the aminimide compound A was changed to the aminimide compound O.

Example 19

An epoxy resin composition was prepared and evaluated for its curability and storage stability at room temperature in the same manner as in Example 1 except that the aminimide compound A was changed to the aminimide composition O2.

Example 20

An epoxy resin composition was prepared and evaluated for its curability and storage stability at room temperature in the same manner as in Example 1 except that the aminimide compound A was changed to the aminimide composition O3.

Example 21

An epoxy resin composition was prepared and evaluated for its curability and storage stability at room temperature in the same manner as in Example 2 except that the aminimide compound A was changed to the aminimide composition O3.

Example 22

An epoxy resin composition was prepared and evaluated for its curability and storage stability at room temperature in the same manner as in Example 1 except that the aminimide compound A was changed to the aminimide compound P.

Example 23

An epoxy resin composition was prepared and evaluated for its curability and storage stability at room temperature in the same manner as in Example 1 except that the aminimide compound A was changed to the aminimide compound Q.

Example 24

An epoxy resin composition was prepared and evaluated for its curability and storage stability at room temperature in the same manner as in Example 1 except that the aminimide compound A was changed to the aminimide composition Q2.

Example 25

An epoxy resin composition was prepared and evaluated for its curability and storage stability at room temperature in the same manner as in Example 1 except that the aminimide compound A was changed to the aminimide compound R.

Example 26

An epoxy resin composition was prepared and evaluated for its curability and storage stability at room temperature in the same manner as in Example 2 except that the aminimide compound A was changed to the aminimide compound R.

Example 27

An epoxy resin composition was prepared and evaluated for its curability and storage stability at room temperature in the same manner as in Example 1 except that the aminimide compound A was changed to the aminimide compound S.

Example 28

An epoxy resin composition was prepared and evaluated for its curability and storage stability at room temperature in the same manner as in Example 2 except that the aminimide compound A was changed to the aminimide compound S.

Example 29

An epoxy resin composition was prepared and evaluated for its curability and storage stability at room temperature in the same manner as in Example 1 except that the aminimide compound A was changed to the aminimide composition S2.

Example 30

An epoxy resin composition was prepared and evaluated for its curability and storage stability at room temperature in the same manner as in Example 2 except that the aminimide compound A was changed to the aminimide composition S2.

Example 31

An epoxy resin composition was prepared and evaluated for its curability and storage stability at room temperature in the same manner as in Example 2 except that the aminimide compound A was changed to the aminimide composition S3.

Example 59

An epoxy resin composition was prepared and evaluated for its curability and storage stability at room temperature in the same manner as in Example 1 except that the aminimide compound A was changed to the aminimide compound I.

Example 60

An epoxy resin composition was prepared and evaluated for its curability and storage stability at room temperature in the same manner as in Example 1 except that the aminimide compound A was changed to the aminimide compound J.

Example 61

An epoxy resin composition was prepared and evaluated for its curability and storage stability at room temperature in the same manner as in Example 1 except that the aminimide compound A was changed to the aminimide compound K.

Comparative Example 1

An epoxy resin composition was prepared and evaluated for its curability and storage stability at room temperature in the same manner as in Example 1 except that the aminimide compound A was changed to DBU ("diazabicycloundecene" manufactured by Tokyo Chemical Industry Co., Ltd.).

Comparative Example 2

An epoxy resin composition was prepared and evaluated for its curability and storage stability at room temperature in the same manner as in Example 1 except that the aminimide compound A was changed to DBU-phenol salt ("U-CAT SA1" manufactured by San-Apro Ltd.).

Comparative Example 3

An epoxy resin composition was prepared and evaluated for its curability and storage stability at room temperature in the same manner as in Example 1 except that the aminimide compound A was changed to the acrylate-imidazole adduct.

Evaluation results of Examples 1 to 31 and 59 to 61 and Comparative Examples 1 to 3 are shown in Tables 2 to 6.

TABLE 2

| | | Unit | Example 1 | Example 2 | Example 3 | Example 4 | Example 5 | Example 6 | Example 7 | Example 8 | Example 9 |
|---|---|---|---|---|---|---|---|---|---|---|---|
| Epoxy resin | BE-186EL | parts by mass | 100 | 100 | 100 | 100 | 100 | 100 | 100 | 100 | 100 |
| Curing agent | Aminimide compound A | parts by mass | 8 | 30 | | | | | | | |
| | Aminimide compound B | parts by mass | | | 10 | 30 | | | | | |
| | Aminimide compound C | parts by mass | | | | | 2 | 8 | | | |
| | Aminimide compound D | parts by mass | | | | | | | 8 | | |
| | Aminimide compound E | parts by mass | | | | | | | | 8 | |
| | Aminimide compound F | parts by mass | | | | | | | | | 8 |
| | Aminimide compound G | parts by mass | | | | | | | | | |
| | Aminimide compound H | parts by mass | | | | | | | | | |
| | Aminimide compound L | parts by mass | | | | | | | | | |
| | Aminimide compound M | parts by mass | | | | | | | | | |
| | Aminimide compound N | parts by mass | | | | | | | | | |
| | Aminimide compound O | parts by mass | | | | | | | | | |
| | Aminimide composition O2 | parts by mass | | | | | | | | | |
| | Aminimide composition O3 | parts by mass | | | | | | | | | |
| | Aminimide compound P | parts by mass | | | | | | | | | |
| | Aminimide compound Q | parts by mass | | | | | | | | | |
| | Aminimide composition Q2 | parts by mass | | | | | | | | | |
| | Aminimide compound R | parts by mass | | | | | | | | | |
| | Aminimide compound S | parts by mass | | | | | | | | | |
| | Aminimide composition S2 | parts by mass | | | | | | | | | |

TABLE 2-continued

| | | Unit | Example 1 | Example 2 | Example 3 | Example 4 | Example 5 | Example 6 | Example 7 | Example 8 | Example 9 |
|---|---|---|---|---|---|---|---|---|---|---|---|
| | Aminimide composition S3 | parts by mass | | | | | | | | | |
| | Aminimide compound I | parts by mass | | | | | | | | | |
| | Aminimide compound J | parts by mass | | | | | | | | | |
| | Aminimide compound K | parts by mass | | | | | | | | | |
| | DBU | parts by mass | | | | | | | | | |
| | U-CAT SA1 | parts by mass | | | | | | | | | |
| | Acrylate-imidazole adduct | parts by mass | | | | | | | | | |
| Curability (1) | | | Δ | ◎ | ○ | ◎ | ◎ | ◎ | ○ | ○ | ○ |
| Storage stability (1) | | | ◎ | ○ | ◎ | ○ | ◎ | ◎ | ◎ | ◎ | ◎ |

TABLE 3

| | | Unit | Example 10 | Example 11 | Example 12 | Example 13 | Example 14 | Example 15 | Example 16 |
|---|---|---|---|---|---|---|---|---|---|
| Epoxy resin | BE-186EL | parts by mass | 100 | 100 | 100 | 100 | 100 | 100 | 100 |
| Curing agent | Aminimide compound A | parts by mass | | | | | | | |
| | Aminimide compound B | parts by mass | | | | | | | |
| | Aminimide compound C | parts by mass | | | | | | | |
| | Aminimide compound D | parts by mass | | | | | | | |
| | Aminimide compound E | parts by mass | | | | | | | |
| | Aminimide compound F | parts by mass | | | | | | | |
| | Aminimide compound G | parts by mass | 8 | | | | | | |
| | Aminimide compound H | parts by mass | | 2 | 8 | | | | |
| | Aminimide compound L | parts by mass | | | | 8 | | | |
| | Aminimide compound M | parts by mass | | | | | 8 | | |
| | Aminimide compound N | parts by mass | | | | | | 8 | 30 |
| | Aminimide compound O | parts by mass | | | | | | | |
| | Aminimide composition O2 | parts by mass | | | | | | | |
| | Aminimide composition O3 | parts by mass | | | | | | | |
| | Aminimide compound P | parts by mass | | | | | | | |
| | Aminimide compound Q | parts by mass | | | | | | | |
| | Aminimide composition Q2 | parts by mass | | | | | | | |
| | Aminimide compound R | parts by mass | | | | | | | |
| | Aminimide compound S | parts by mass | | | | | | | |
| | Aminimide composition S2 | parts by mass | | | | | | | |
| | Aminimide composition S3 | parts by mass | | | | | | | |
| | Aminimide compound I | parts by mass | | | | | | | |
| | Aminimide compound J | parts by mass | | | | | | | |
| | Aminimide compound K | parts by mass | | | | | | | |

TABLE 3-continued

| | | Unit | Example 10 | Example 11 | Example 12 | Example 13 | Example 14 | Example 15 | Example 16 |
|---|---|---|---|---|---|---|---|---|---|
| | DBU | parts by mass | | | | | | | |
| | U-CAT SA1 | parts by mass | | | | | | | |
| | Acrylate-imidazole adduct | parts by mass | | | | | | | |
| | Curability (1) | | ◎ | ○ | ◎ | ◎ | ◎ | ◎ | ◎ |
| | Storage stability (1) | | ◎ | ◎ | ◎ | ◎ | ◎ | ◎ | ◎ |

TABLE 4

| | | Unit | Example 17 | Example 18 | Example 19 | Example 20 | Example 21 | Example 22 | Example 23 | Example 24 | Example 25 |
|---|---|---|---|---|---|---|---|---|---|---|---|
| Epoxy resin | BE-186EL | parts by mass | 100 | 100 | 100 | 100 | 100 | 100 | 100 | 100 | 100 |
| Curing agent | Aminimide compound A | parts by mass | | | | | | | | | |
| | Aminimide compound B | parts by mass | | | | | | | | | |
| | Aminimide compound C | parts by mass | | | | | | | | | |
| | Aminimide compound D | parts by mass | | | | | | | | | |
| | Aminimide compound E | parts by mass | | | | | | | | | |
| | Aminimide compound F | parts by mass | | | | | | | | | |
| | Aminimide compound G | parts by mass | | | | | | | | | |
| | Aminimide compound H | parts by mass | | | | | | | | | |
| | Aminimide compound L | parts by mass | | | | | | | | | |
| | Aminimide compound M | parts by mass | | | | | | | | | |
| | Aminimide compound N | parts by mass | | | | | | | | | |
| | Aminimide compound O | parts by mass | 8 | 30 | | | | | | | |
| | Aminimide composition O2 | parts by mass | | | 8 | | | | | | |
| | Aminimide composition O3 | parts by mass | | | | 8 | 30 | | | | |
| | Aminimide compound P | parts by mass | | | | | | 8 | | | |
| | Aminimide compound Q | parts by mass | | | | | | | 8 | | |
| | Aminimide composition Q2 | parts by mass | | | | | | | | 8 | |
| | Aminimide compound R | parts by mass | | | | | | | | | 8 |
| | Aminimide compound S | parts by mass | | | | | | | | | |
| | Aminimide composition S2 | parts by mass | | | | | | | | | |
| | Aminimide composition S3 | parts by mass | | | | | | | | | |
| | Aminimide compound I | parts by mass | | | | | | | | | |
| | Aminimide compound J | parts by mass | | | | | | | | | |
| | Aminimide compound K | parts by mass | | | | | | | | | |
| | DBU | parts by mass | | | | | | | | | |
| | U-CAT SA1 | parts by mass | | | | | | | | | |
| | Acrylate-imidazole adduct | parts by mass | | | | | | | | | |

TABLE 4-continued

| | Unit | Example 17 | Example 18 | Example 19 | Example 20 | Example 21 | Example 22 | Example 23 | Example 24 | Example 25 |
|---|---|---|---|---|---|---|---|---|---|---|
| Curability (1) | | ◎ | ◎ | ○ | ◎ | ◎ | ○ | ◎ | ◎ | ○ |
| Storage stability (1) | | ◎ | ◎ | ◎ | ◎ | ◎ | ◎ | ◎ | ◎ | ◎ |

TABLE 5

| | | Unit | Example 26 | Example 27 | Example 28 | Example 29 | Example 30 | Example 31 |
|---|---|---|---|---|---|---|---|---|
| Epoxy resin | BE-186EL | parts by mass | 100 | 100 | 100 | 100 | 100 | 100 |
| Curing agent | Aminimide compound A | parts by mass | | | | | | |
| | Aminimide compound B | parts by mass | | | | | | |
| | Aminimide compound C | parts by mass | | | | | | |
| | Aminimide compound D | parts by mass | | | | | | |
| | Aminimide compound E | parts by mass | | | | | | |
| | Aminimide compound F | parts by mass | | | | | | |
| | Aminimide compound G | parts by mass | | | | | | |
| | Aminimide compound H | parts by mass | | | | | | |
| | Aminimide compound L | parts by mass | | | | | | |
| | Aminimide compound M | parts by mass | | | | | | |
| | Aminimide compound N | parts by mass | | | | | | |
| | Aminimide compound O | parts by mass | | | | | | |
| | Aminimide composition O2 | parts by mass | | | | | | |
| | Aminimide composition O3 | parts by mass | | | | | | |
| | Aminimide compound P | parts by mass | | | | | | |
| | Aminimide compound Q | parts by mass | | | | | | |
| | Aminimide composition Q2 | parts by mass | | | | | | |
| | Aminimide compound R | parts by mass | 30 | | | | | |
| | Aminimide compound S | parts by mass | | 8 | 30 | | | |
| | Aminimide composition S2 | parts by mass | | | | 8 | 30 | |
| | Aminimide composition S3 | parts by mass | | | | | | 30 |
| | Aminimide compound I | parts by mass | | | | | | |
| | Aminimide compound J | parts by mass | | | | | | |
| | Aminimide compound K | parts by mass | | | | | | |
| | DBU | parts by mass | | | | | | |
| | U-CAT SA1 | parts by mass | | | | | | |
| | Acrylate-imidazole adduct | parts by mass | | | | | | |
| Curability (1) | | | ○ | ○ | ○ | ○ | ○ | ○ |
| Storage stability (1) | | | ◎ | ◎ | ◎ | ◎ | ◎ | ◎ |

TABLE 6

| | | Unit | Example 59 | Example 60 | Example 61 | Comparative Example 1 | Comparative Example 2 | Comparative Example 3 |
|---|---|---|---|---|---|---|---|---|
| Epoxy resin | BE-186EL | parts by mass | 100 | 100 | 100 | 100 | 100 | 100 |
| Curing agent | Aminimide compound A | parts by mass | | | | | | |
| | Aminimide compound B | parts by mass | | | | | | |
| | Aminimide compound C | parts by mass | | | | | | |
| | Aminimide compound D | parts by mass | | | | | | |
| | Aminimide compound E | parts by mass | | | | | | |
| | Aminimide compound F | parts by mass | | | | | | |
| | Aminimide compound G | parts by mass | | | | | | |
| | Aminimide compound H | parts by mass | | | | | | |
| | Aminimide compound L | parts by mass | | | | | | |
| | Aminimide compound M | parts by mass | | | | | | |
| | Aminimide compound N | parts by mass | | | | | | |
| | Aminimide compound O | parts by mass | | | | | | |
| | Aminimide composition O2 | parts by mass | | | | | | |
| | Aminimide composition O3 | parts by mass | | | | | | |
| | Aminimide compound P | parts by mass | | | | | | |
| | Aminimide compound Q | parts by mass | | | | | | |
| | Aminimide composition Q2 | parts by mass | | | | | | |
| | Aminimide compound R | parts by mass | | | | | | |
| | Aminimide compound S | parts by mass | | | | | | |
| | Aminimide composition S2 | parts by mass | | | | | | |
| | Aminimide composition S3 | parts by mass | | | | | | |
| | Aminimide compound I | parts by mass | 8 | | | | | |
| | Aminimide compound J | parts by mass | | 8 | | | | |
| | Aminimide compound K | parts by mass | | | 8 | | | |
| | DBU | parts by mass | | | | 8 | | |
| | U-CAT SA1 | parts by mass | | | | | 8 | |
| | Acrylate-imidazole adduct | parts by mass | | | | | | 8 |
| Curability (1) | | | ○ | Δ | ◎ | ◎ | ◎ | ◎ |
| Storage stability (1) | | | ◎ | Δ | ◎ | X | X | X |

[Preparation (2) of Epoxy Resin Composition]

In each of the epoxy resin compositions prepared in Examples and Comparative Examples given below, the following epoxy resin and acid anhydride were used as starting materials.

Epoxy resin: Chang Chun Plastics Co., Ltd "BE-186EL"

Acid anhydride: "HN-5500" manufactured by Hitachi Chemical Co., Ltd.

For mixing starting materials, the starting materials were added such that the equivalent ratio between an epoxy group in the epoxy resin and an acid anhydride group in the acid anhydride was acid anhydride group/epoxy group=1.00.

Each starting material was added in accordance with the amount of the starting material blended shown in Tables 7 to 9 per 100 parts by mass of the epoxy resin.

The epoxy resin and the aminimide compound, the aminimide composition, DBU, U-CAT SA1, or the acrylate-imidazole adduct (hereinafter, also referred to as the aminimide compound, etc.) were placed in a plastic stirring container and mixed by stirring using a rotation/revolution mixer ("ARE-310" manufactured by Thinky Corp.) so that the epoxy resin and the aminimide compound, etc. were premixed. Subsequently, a predetermined amount of the acid anhydride was added to the premixture and further mixed by stirring to prepare an epoxy resin composition.

[Method (2) for Evaluating Curability]

In the method (2) for evaluating curability, the prepared epoxy resin composition was heated under conditions given below and evaluated. The curability was determined as follows: "◎" when a temperature that reached 100 Pa·s was +15° C. as compared with the case of using DBU as a curing accelerator; "○" when this temperature was +15° C. or more and less than +30° C.; "Δ" when this temperature was +30° C. or more and less than +45° C.; and "X" when this temperature was +45° C. or more.

<Measurement Conditions>

Apparatus: Viscoelasticity measurement apparatus ("HAAKE MARS" manufactured by Thermo Fisher Scientific, Inc.)

Sample mass: Approximately 0.5 mL

Plate shape: Parallel

Measurement mode: Constant shear rate ($d\gamma/dt=1.0\ s^{-1}$)

Measurement temperature: 40° C. to 240° C.

Temperature increase rate: 5° C./min

[Method (2) for Evaluating Storage Stability]

In the method (2) for evaluating storage stability, the viscosity at 25° C. of the epoxy resin composition immediately after preparation was defined as "$\eta 1$", and the viscosity at 25° C. of the epoxy resin composition preserved for 3 days in a thermostat bath of 25° C. was defined as "$\eta 2$". A value calculated according to $\eta 2/\eta 1$ was determined as a viscosity increase ratio. The storage stability was determined as follows: "◎" when the viscosity increase ratio was less than 3.0-fold; "○" when the viscosity increase ratio was 3.0-fold or more and less than 7.0-fold; "Δ" when the viscosity increase ratio was 7.0-fold or more and less than 10.0-fold; and "X" when the viscosity increase ratio was 10.0-fold or more.

[Method for Evaluating Prepreg Surface Smoothness]

Carbon fiber cloth ("TORAYCA CLOTH CO6343" manufactured by Toray Industries, Inc.) (basis weight: 198 $g/m^2$) was impregnated with the prepared epoxy resin composition for 5 minutes and heated for 10 minutes in an oven of 170° C. to prepare a prepreg. Then, the surface state of the obtained prepreg was observed. The surface state was determined as follows: "○" for smooth surface; and "X" when surface irregularities ascribable to voids or the like were observed.

[Method for Evaluating Prepreg Tackiness]

Carbon fiber cloth ("TORAYCA CLOTH CO6343" manufactured by Toray Industries, Inc.) (basis weight: 198 $g/m^2$) was impregnated with the prepared epoxy resin composition for 5 minutes and heated for 10 minutes in an oven of 170° C. to prepare a prepreg. Then, the tackiness of the obtained prepreg was confirmed. The tackiness was determined as follows: "○" when tack was absent; and "X" when tack was present.

[Method for Evaluating Penetration]

Carbon fiber cloth ("TORAYCA CLOTH CO6343" manufactured by Toray Industries, Inc.) (basis weight: 198 $g/m^2$) was tucked as filter cloth into a pressure filter, and the prepared epoxy resin composition was pressure-filtered with 0.2 L/min of nitrogen at room temperature. 10 mg of the epoxy resin composition obtained as a filtrate was weighed into an aluminum container of a differential scanning calorimeter ("DSC220C" manufactured by Seiko Instruments Inc. (SII)), heated for 1.5 hours in an oven of 180° C., and then quenched. A reaction rate was calculated from change in DSC calorific value between before and after filtration. The penetration was determined as follows: "○" when the reaction rate was 95% or more; and "X" when the reaction rate was less than 95%.

When the aminimide compound, etc. was used as a curing accelerator in this evaluation, it was confirmed that in the case of a curing accelerator excellent in penetration, the amount of the curing accelerator in the epoxy resin composition did not differ between before and after pressure filtration and the desired reactivity was obtained. On the other hand, it was confirmed that in the case of a curing accelerator inferior in penetration, at least a portion of the curing accelerator was trapped in the carbon fiber cloth so that the amount of the curing accelerator in the epoxy resin composition was decreased after pressure filtration and the desired reactivity was not obtained.

Example 32

20 g of the epoxy resin ("BE-186EL" manufactured by Chang Chun Plastics Co., Ltd) and 0.6 g of the aminimide compound A were placed in a plastic stirring container and mixed by stirring using a rotation/revolution mixer ("ARE-310" manufactured by Thinky Corp.). Subsequently, 17.9 g of the acid anhydride ("HN-5500" manufactured by Hitachi Chemical Co., Ltd.) was added thereto and further mixed by stirring to prepare an epoxy resin composition. The curability was evaluated by the method (2) for evaluating curability, and the storage stability at room temperature was evaluated by the method (2) for evaluating storage stability. Also, the prepreg surface smoothness, the prepreg tackiness, and the penetration were also evaluated.

Example 33

An epoxy resin composition was prepared and evaluated for its curability, storage stability at room temperature, prepreg surface smoothness, prepreg tackiness, and penetration in the same manner as in Example 32 except that the amount of the aminimide compound A added was changed to 3.6 g.

Example 34

An epoxy resin composition was prepared and evaluated for its curability, storage stability at room temperature, prepreg surface smoothness, prepreg tackiness, and penetration in the same manner as in Example 32 except that the aminimide compound A was changed to the aminimide compound B.

Example 35

An epoxy resin composition was prepared and evaluated for its curability, storage stability at room temperature, prepreg surface smoothness, prepreg tackiness, and penetration in the same manner as in Example 32 except that: the aminimide compound A was changed to the aminimide compound B; and the amount of the aminimide compound B added was changed to 3.6 g.

Example 36

An epoxy resin composition was prepared and evaluated for its curability, storage stability at room temperature, prepreg surface smoothness, prepreg tackiness, and penetration in the same manner as in Example 32 except that: the aminimide compound A was changed to the aminimide compound B; and the amount of the aminimide compound B added was changed to 4.8 g.

Example 37

An epoxy resin composition was prepared and evaluated for its curability, storage stability at room temperature, prepreg surface smoothness, prepreg tackiness, and penetration in the same manner as in Example 32 except that: the aminimide compound A was changed to the aminimide compound C; and the amount of the aminimide compound C added was changed to 0.2 g.

Example 38

An epoxy resin composition was prepared and evaluated for its curability, storage stability at room temperature, prepreg surface smoothness, prepreg tackiness, and penetration in the same manner as in Example 32 except that the aminimide compound A was changed to the aminimide compound C.

Example 39

An epoxy resin composition was prepared and evaluated for its curability, storage stability at room temperature, prepreg surface smoothness, prepreg tackiness, and penetration in the same manner as in Example 32 except that the aminimide compound A was changed to the aminimide compound D.

Example 40

An epoxy resin composition was prepared and evaluated for its curability, storage stability at room temperature, prepreg surface smoothness, prepreg tackiness, and penetration in the same manner as in Example 32 except that the aminimide compound A was changed to the aminimide compound E.

Example 41

An epoxy resin composition was prepared and evaluated for its curability, storage stability at room temperature, prepreg surface smoothness, prepreg tackiness, and penetration in the same manner as in Example 32 except that the aminimide compound A was changed to the aminimide compound F.

Example 42

An epoxy resin composition was prepared and evaluated for its curability, storage stability at room temperature, prepreg surface smoothness, prepreg tackiness, and penetration in the same manner as in Example 32 except that: the aminimide compound A was changed to the aminimide compound F; and the amount of the aminimide compound F added was changed to 2.0 g.

Example 43

An epoxy resin composition was prepared and evaluated for its curability, storage stability at room temperature, prepreg surface smoothness, prepreg tackiness, and penetration in the same manner as in Example 32 except that the aminimide compound A was changed to the aminimide compound G.

Example 44

An epoxy resin composition was prepared and evaluated for its curability, storage stability at room temperature, prepreg surface smoothness, prepreg tackiness, and penetration in the same manner as in Example 32 except that: the aminimide compound A was changed to the aminimide compound H; and the amount of the aminimide compound H added was changed to 0.2 g.

Example 45

An epoxy resin composition was prepared and evaluated for its curability, storage stability at room temperature, prepreg surface smoothness, prepreg tackiness, and penetration in the same manner as in Example 32 except that the aminimide compound A was changed to the aminimide compound H.

Example 46

An epoxy resin composition was prepared and evaluated for its curability, storage stability at room temperature, prepreg surface smoothness, prepreg tackiness, and penetration in the same manner as in Example 32 except that the aminimide compound A was changed to the aminimide compound L.

Example 47

An epoxy resin composition was prepared and evaluated for its curability, storage stability at room temperature, prepreg surface smoothness, prepreg tackiness, and penetration in the same manner as in Example 32 except that the aminimide compound A was changed to the aminimide compound M.

Example 48

An epoxy resin composition was prepared and evaluated for its curability, storage stability at room temperature, prepreg surface smoothness, prepreg tackiness, and penetration in the same manner as in Example 32 except that the aminimide compound A was changed to the aminimide compound N.

Example 49

An epoxy resin composition was prepared and evaluated for its curability, storage stability at room temperature, prepreg surface smoothness, prepreg tackiness, and penetration in the same manner as in Example 32 except that the aminimide compound A was changed to the aminimide compound O.

Example 50

An epoxy resin composition was prepared and evaluated for its curability, storage stability at room temperature, prepreg surface smoothness, prepreg tackiness, and penetration in the same manner as in Example 32 except that the aminimide compound A was changed to the aminimide composition O2.

Example 51

An epoxy resin composition was prepared and evaluated for its curability, storage stability at room temperature, prepreg surface smoothness, prepreg tackiness, and penetration in the same manner as in Example 32 except that the aminimide compound A was changed to the aminimide composition O3.

Example 52

An epoxy resin composition was prepared and evaluated for its curability, storage stability at room temperature, prepreg surface smoothness, prepreg tackiness, and penetration in the same manner as in Example 32 except that the aminimide compound A was changed to the aminimide compound P.

Example 53

An epoxy resin composition was prepared and evaluated for its curability, storage stability at room temperature, prepreg surface smoothness, prepreg tackiness, and penetration in the same manner as in Example 32 except that the aminimide compound A was changed to the aminimide compound Q.

Example 54

An epoxy resin composition was prepared and evaluated for its curability, storage stability at room temperature, prepreg surface smoothness, prepreg tackiness, and penetration in the same manner as in Example 32 except that the aminimide compound A was changed to the aminimide composition Q2.

Example 55

An epoxy resin composition was prepared and evaluated for its curability, storage stability at room temperature, prepreg surface smoothness, prepreg tackiness, and penetration in the same manner as in Example 32 except that the aminimide compound A was changed to the aminimide compound R.

Example 56

An epoxy resin composition was prepared and evaluated for its curability, storage stability at room temperature, prepreg surface smoothness, prepreg tackiness, and penetration in the same manner as in Example 32 except that the aminimide compound A was changed to the aminimide compound S.

Example 57

An epoxy resin composition was prepared and evaluated for its curability, storage stability at room temperature, prepreg surface smoothness, prepreg tackiness, and penetration in the same manner as in Example 32 except that the aminimide compound A was changed to the aminimide composition S2.

Example 58

An epoxy resin composition was prepared and evaluated for its curability, storage stability at room temperature, prepreg surface smoothness, prepreg tackiness, and penetration in the same manner as in Example 32 except that the aminimide compound A was changed to the aminimide composition S3.

Example 62

An epoxy resin composition was prepared and evaluated for its curability, storage stability at room temperature, prepreg surface smoothness, prepreg tackiness, and penetration in the same manner as in Example 32 except that the aminimide compound A was changed to the aminimide compound I.

Example 63

An epoxy resin composition was prepared and evaluated for its curability, storage stability at room temperature, prepreg surface smoothness, prepreg tackiness, and penetration in the same manner as in Example 32 except that the aminimide compound A was changed to the aminimide compound J.

Example 64

An epoxy resin composition was prepared and evaluated for its curability, storage stability at room temperature, prepreg surface smoothness, prepreg tackiness, and penetration in the same manner as in Example 32 except that the aminimide compound A was changed to the aminimide compound K.

Comparative Example 4

An epoxy resin composition was prepared and evaluated for its curability, storage stability at room temperature, prepreg surface smoothness, prepreg tackiness, and penetration in the same manner as in Example 32 except that the aminimide compound A was changed to DBU ("diazabicycloundecene" manufactured by Tokyo Chemical Industry Co., Ltd.).

Comparative Example 5

An epoxy resin composition was prepared and evaluated for its curability, storage stability at room temperature, prepreg surface smoothness, prepreg tackiness, and penetration in the same manner as in Example 32 except that the aminimide compound A was changed to DBU-phenol salt ("U-CAT SA1" manufactured by San-Apro Ltd.).

Comparative Example 6

An epoxy resin composition was prepared and evaluated for its curability, storage stability at room temperature, prepreg surface smoothness, prepreg tackiness, and penetration in the same manner as in Example 32 except that the aminimide compound A was changed to the acrylate-imidazole adduct.

Comparative Example 7

An epoxy resin composition was prepared and evaluated for its curability, storage stability at room temperature, prepreg surface smoothness, prepreg tackiness, and penetration in the same manner as in Example 32 except that the aminimide compound A was changed to a powder amine curing agent ("AJICURE PN-23" manufactured by Ajinomoto Fine-Techno Co., Inc.).

Evaluation results of Examples 32 to 58 and 62 to 64 and Comparative Examples 4 to 7 are shown in Tables 7 to 9.

TABLE 7

| | | Unit | Example 32 | Example 33 | Example 34 | Example 35 | Example 36 | Example 37 | Example 38 | Example 39 | Example 40 | Example 41 | Example 42 | Example 43 |
|---|---|---|---|---|---|---|---|---|---|---|---|---|---|---|
| Epoxy resin | BE-186EL | parts by mass | 100 | 100 | 100 | 100 | 100 | 100 | 100 | 100 | 100 | 100 | 100 | 100 |
| Acid anhydride | HN-5500 | parts by mass | 89.5 | 89.5 | 89.5 | 89.5 | 89.5 | 89.5 | 89.5 | 89.5 | 89.5 | 89.5 | 89.5 | 89.5 |
| Curing accelerator | Aminimide compound A | parts by mass | 3 | 18 | | | | | | | | | | |
| | Aminimide compound B | parts by mass | | | 3 | 18 | 24 | | | | | | | |
| | Aminimide compound C | parts by mass | | | | | | 1 | 3 | | | | | |
| | Aminimide compound D | parts by mass | | | | | | | | 3 | | | | |
| | Aminimide compound E | parts by mass | | | | | | | | | 3 | | | |
| | Aminimide compound F | parts by mass | | | | | | | | | | 3 | 10 | |
| | Aminimide compound G | parts by mass | | | | | | | | | | | | 3 |
| | Aminimide compound H | parts by mass | | | | | | | | | | | | |
| | Aminimide compound L | parts by mass | | | | | | | | | | | | |
| | Aminimide compound M | parts by mass | | | | | | | | | | | | |
| | Aminimide compound N | parts by mass | | | | | | | | | | | | |
| | Aminimide compound O | parts by mass | | | | | | | | | | | | |
| | Aminimide composition O2 | parts by mass | | | | | | | | | | | | |
| | Aminimide composition O3 | parts by mass | | | | | | | | | | | | |
| | Aminimide compound P | parts by mass | | | | | | | | | | | | |
| | Aminimide compound Q | parts by mass | | | | | | | | | | | | |
| | Aminimide composition Q2 | parts by mass | | | | | | | | | | | | |
| | Aminimide compound R | parts by mass | | | | | | | | | | | | |
| | Aminimide compound S | parts by mass | | | | | | | | | | | | |
| | Aminimide composition S2 | parts by mass | | | | | | | | | | | | |
| | Aminimide composition S3 | parts by mass | | | | | | | | | | | | |
| | Aminimide compound I | parts by mass | | | | | | | | | | | | |
| | Aminimide compound J | parts by mass | | | | | | | | | | | | |
| | Aminimide compound K | parts by mass | | | | | | | | | | | | |
| | DBU | parts by mass | | | | | | | | | | | | |
| | U-CAT SA1 | parts by mass | | | | | | | | | | | | |
| | Acrylate-imidazole adduct | parts by mass | | | | | | | | | | | | |
| Curability (2) | | | ○ | ◎ | ○ | ◎ | ◎ | ○ | ◎ | Δ | ○ | Δ | ○ | ○ |
| Storage stability (2) | | | ◎ | ○ | ◎ | ○ | Δ | ◎ | ◎ | ◎ | ◎ | ○ | ○ | ○ |
| Prepreg surface smoothness | | | ○ | ○ | ○ | ○ | ○ | ○ | ○ | ○ | ○ | ○ | ○ | ○ |
| Prepreg tackiness | | | ○ | ○ | ○ | ○ | ○ | ○ | ○ | ○ | ○ | ○ | ○ | ○ |
| Penetration | | | ○ | ○ | ○ | ○ | ○ | ○ | ○ | ○ | ○ | ○ | ○ | ○ |

TABLE 8

| | | Unit | Example 44 | Example 45 | Example 46 | Example 47 | Example 48 | Example 49 | Example 50 | Example 51 | Example 52 | Example 53 | Example 54 | Example 55 |
|---|---|---|---|---|---|---|---|---|---|---|---|---|---|---|
| Epoxy resin | BE-186EL | parts by mass | 100 | 100 | 100 | 100 | 100 | 100 | 100 | 100 | 100 | 100 | 100 | 100 |
| Acid anhydride | HN-5500 | parts by mass | 89.5 | 89.5 | 89.5 | 89.5 | 89.5 | 89.5 | 89.5 | 89.5 | 89.5 | 89.5 | 89.5 | 89.5 |
| Curing accelerator | Aminimide compound A | parts by mass | | | | | | | | | | | | |
| | Aminimide compound B | parts by mass | | | | | | | | | | | | |
| | Aminimide compound C | parts by mass | | | | | | | | | | | | |
| | Aminimide compound D | parts by mass | | | | | | | | | | | | |
| | Aminimide compound E | parts by mass | | | | | | | | | | | | |
| | Aminimide compound F | parts by mass | | | | | | | | | | | | |
| | Aminimide compound G | parts by mass | | | | | | | | | | | | |
| | Aminimide compound H | parts by mass | 1 | 3 | | | | | | | | | | |
| | Aminimide compound L | parts by mass | | | 3 | | | | | | | | | |
| | Aminimide compound M | parts by mass | | | | 3 | | | | | | | | |
| | Aminimide compound N | parts by mass | | | | | 3 | | | | | | | |
| | Aminimide compound O | parts by mass | | | | | | 3 | | | | | | |
| | Aminimide composition O2 | parts by mass | | | | | | | 3 | | | | | |
| | Aminimide composition O3 | parts by mass | | | | | | | | 3 | | | | |
| | Aminimide compound P | parts by mass | | | | | | | | | 3 | | | |
| | Aminimide compound Q | parts by mass | | | | | | | | | | 3 | | |
| | Aminimide composition Q2 | parts by mass | | | | | | | | | | | 3 | |
| | Aminimide compound R | parts by mass | | | | | | | | | | | | 3 |
| | Aminimide compound S | parts by mass | | | | | | | | | | | | |
| | Aminimide composition S2 | parts by mass | | | | | | | | | | | | |
| | Aminimide composition S3 | parts by mass | | | | | | | | | | | | |
| | Aminimide compound I | parts by mass | | | | | | | | | | | | |
| | Aminimide compound J | parts by mass | | | | | | | | | | | | |
| | Aminimide compound K | parts by mass | | | | | | | | | | | | |
| | DBU | parts by mass | | | | | | | | | | | | |
| | U-CAT SA1 | parts by mass | | | | | | | | | | | | |
| | Acrylate-imidazole adduct | parts by mass | | | | | | | | | | | | |
| Curability (2) | | | ○ | ◎ | ◎ | ◎ | ○ | ○ | ○ | ○ | ○ | ○ | ○ | Δ |
| Storage stability (2) | | | ◎ | ◎ | ○ | ○ | ◎ | ◎ | ◎ | ◎ | ◎ | ◎ | ◎ | ◎ |
| Prepreg surface smoothness | | | ○ | ○ | ○ | ○ | ○ | ○ | ○ | ○ | ○ | ○ | ○ | ○ |
| Prepreg tackiness | | | ○ | ○ | ◎ | ◎ | ○ | ○ | ○ | ○ | ○ | ○ | ○ | ○ |
| Penetration | | | ○ | ○ | ○ | ○ | ○ | ○ | ○ | ○ | ○ | Δ | ○ | ○ |

TABLE 9

| | | Unit | Example 56 | Example 57 | Example 58 | Example 62 | Example 63 | Example 64 | Comparative Example 4 | Comparative Example 5 | Comparative Example 6 | Comparative Example 7 |
|---|---|---|---|---|---|---|---|---|---|---|---|---|
| Epoxy resin | BE-186EL | parts by mass | 100 | 100 | 100 | 100 | 100 | 100 | 100 | 100 | 100 | 100 |
| Acid anhydride | HN-5500 | parts by mass | 89.5 | 89.5 | 89.5 | 89.5 | 89.5 | 89.5 | 89.5 | 89.5 | 89.5 | 89.5 |
| Curing accelerator | Aminimide compound A | parts by mass | | | | | | | | | | |
| | Aminimide compound B | parts by mass | | | | | | | | | | |
| | Aminimide compound C | parts by mass | | | | | | | | | | |
| | Aminimide compound D | parts by mass | | | | | | | | | | |
| | Aminimide compound E | parts by mass | | | | | | | | | | |
| | Aminimide compound F | parts by mass | | | | | | | | | | |
| | Aminimide compound G | parts by mass | | | | | | | | | | |
| | Aminimide compound H | parts by mass | | | | | | | | | | |
| | Aminimide compound L | parts by mass | | | | | | | | | | |
| | Aminimide compound M | parts by mass | | | | | | | | | | |
| | Aminimide compound N | parts by mass | | | | | | | | | | |
| | Aminimide compound O | parts by mass | | | | | | | | | | |
| | Aminimide composition O2 | parts by mass | | | | | | | | | | |
| | Aminimide composition O3 | parts by mass | | | | | | | | | | |
| | Aminimide compound P | parts by mass | | | | | | | | | | |
| | Aminimide compound Q | parts by mass | | | | | | | | | | |
| | Aminimide composition Q2 | parts by mass | | | | | | | | | | |
| | Aminimide compound R | parts by mass | | | | | | | | | | |
| | Aminimide compound S | parts by mass | 3 | | | | | | | | | |
| | Aminimide composition S2 | parts by mass | | 3 | | | | | | | | |
| | Aminimide composition S3 | parts by mass | | | 3 | | | | | | | |
| | Aminimide compound I | parts by mass | | | | 2 | | | | | | |
| | Aminimide compound J | parts by mass | | | | | 2 | | | | | |
| | Aminimide compound K | parts by mass | | | | | | 2 | | | | |
| | DBU | parts by mass | | | | | | | 3 | | | |
| | U-CAT SA1 | parts by mass | | | | | | | | 3 | | |
| | Acrylate-imidazole adduct | parts by mass | | | | | | | | | 3 | |
| | AJICURE PN-23 | parts by mass | | | | | | | | | | 2 |
| Curability (2) | | | ○ | ○ | ○ | ○ | Δ | ○ | ◎ | ◎ | ◎ | ◎ |
| Storage stability (2) | | | ◎ | ◎ | ◎ | ◎ | ◎ | ○ | X | X | X | X |
| Prepreg surface smoothness | | | ○ | ○ | ○ | ○ | ○ | ○ | ○ | ○ | ○ | X |
| Prepreg tackiness | | | ○ | ○ | ○ | ○ | ○ | ○ | ○ | ○ | ○ | ○ |
| Penetration | | | ○ | ○ | ○ | ○ | ○ | ○ | ○ | ○ | ○ | X |

From the results of Tables 1 to 9, the epoxy resin compositions of Examples 1 to 64 using the aminimide compounds or the aminimide compositions A to S3 obtained in Synthesis Examples 1 to 24 were confirmed to be excellent in curability and storage stability.

From the results of Tables 7 to 9, the epoxy resin compositions of Examples 32 to 64 using the aminimide compounds or the aminimide compositions A to S3 obtained in Synthesis Examples 1 to 24 were confirmed to be also excellent in penetration and to exert favorable prepreg characteristics.

On the other hand, the epoxy resin compositions of Comparative Examples 1 to 7 were confirmed to be inferior in storage stability at room temperature, though being excellent in curability.

[Method for Measuring Lap-Shear Strength]

Tensile lap-shear strength against a steel plate was measured in accordance with JIS K6850.

Shear adhesion was evaluated using epoxy resin compositions of Examples 65 to 68 prepared as described below.

Examples 65 to 76

Bisphenol A-type epoxy resin: Chang Chun Plastics Co., Ltd "BE-186EL", bisphenol F-type epoxy resin: "jER806" manufactured by Mitsubishi Chemical Corp., bisphenol F-type epoxy resin: glycidyl amine-based epoxy resin "jER630" manufactured by Mitsubishi Chemical Corp., and naphthalene-type epoxy resin: "HP-4032D" manufactured by DIC Corp. were used as epoxy resins for the epoxy resin compositions.

A predetermined aminimide compound shown in Table 10 below was added at 20 parts by mass per 100 parts by mass of the whole epoxy resin. Acrylate-imidazole was added at 10 parts by mass. The epoxy resin and the aminimide compound were placed in a plastic stirring container and mixed by stirring using a rotation/revolution mixer ("ARE-310" manufactured by Thinky Corp.) to prepare an epoxy resin composition.

The epoxy resin composition prepared as mentioned above was applied to between two steel plate test pieces (SPCC-SB; manufactured by Standard Test Piece Co., Ltd.) at an adhesion area of 12.5 mm×5 mm, and then heated at a set temperature of 150° C. for 2 hours in a heating furnace for thermal curing adhesion to obtain a test piece. The tensile lap-shear strength of the obtained test piece was measured in a constant temperature and humidity room of 23° C. and 50% RH using AUTOGRAPH AGS-X 5 kN (manufactured by Shimadzu Corp.). A median value of the obtained values was regarded as tensile lap-shear strength against the steel plate base materials.

TABLE 10

| | | The number of $N^-$—$N^+$ in one molecule | Example 65 | Example 66 | Example 67 | Example 68 | Example 69 | Example 70 |
|---|---|---|---|---|---|---|---|---|
| Curing agent | Aminimide compound O | 2 | 20 | 20 | | | | |
| | Aminimide compound N | 1 | | | 20 | | | |
| | Aminimide compound M | 2 | | | | 20 | 20 | |
| | Aminimide compound C | 1 | | | | | | 20 |
| | Acrylate-imidazole adduct | 0 | | | | | | |
| Epoxy resin | BE-186EL | — | 100 | | 100 | 100 | | 100 |
| | jER806 | — | | 100 | | | 100 | |
| | jER630 | — | | | | | | |
| | HP-4032D | — | | | | | | |
| | Lap-shear strength MPa | | 27.7 | 26.5 | 21.7 | 22.4 | 24.3 | 11.8 |

| | | Example 71 | Example 72 | Example 73 | Example 74 | Example 75 | Example 76 |
|---|---|---|---|---|---|---|---|
| Curing agent | Aminimide compound O | 20 | 20 | | | | |
| | Aminimide compound N | | | 20 | 20 | | |
| | Aminimide compound M | | | | | | |
| | Aminimide compound C | | | | | | |
| | Acrylate-imidazole adduct | | | | | 10 | 10 |
| Epoxy resin | BE-186EL | | | | | | |
| | jER806 | 50 | 50 | 50 | 50 | 100 | 50 |
| | jER630 | 50 | 25 | 50 | 25 | | 50 |
| | HP-4032D | | 25 | | 25 | | |
| | Lap-shear strength MPa | 22.9 | 24.1 | 21.1 | 23.3 | 14.0 | 10.7 |

From the measurement results shown in Table 10, the structures having a plurality of —$N^-$—$N^+$ bonds in one molecule (aminimide compounds O, M, etc.) were found to have higher lap-shear strength than that of the structures having almost the same —N—N— decomposition temperature (start temperature and peak top temperature) thereas and having one —$N^-$—$N^+$ bond, under the same curing conditions. This is presumably because in the case of having a plurality of —$N^-$—$N^+$ bonds in one molecule, the amount of the active ingredient per mass of the curing agent is increased.

The present application is based on the Japanese patent application (Japanese Patent Application No. 2020-121122) filed in the Japan Patent Office on Jul. 15, 2020, the contents of which are incorporated herein by reference.

INDUSTRIAL APPLICABILITY

The aminimide compound and the epoxy resin composition of the present invention have industrial applicability as, for example, encapsulants, adhesives, print substrate materials, coating materials, composite materials, semiconductor encapsulants such as underfills and moldings, conductive adhesives such as ACF, printed circuit boards such as solder resists and coverlay films, and composite materials such as prepregs prepared by the impregnation of glass fibers, carbon fibers, or the like.

The invention claimed is:

1. An aminimide compound represented by the following formula (1), (2) or (3):

(1)

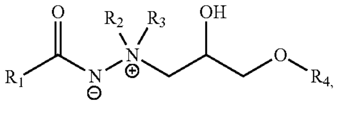

(2)

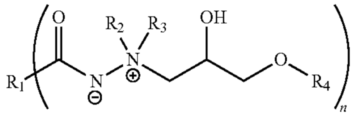

, or (3)

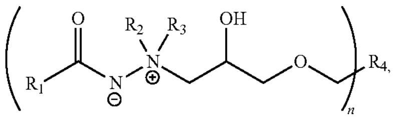

wherein, in the formula (1) or (2), each $R_1$ independently represents a hydrogen atom, or a monovalent or n-valent organic group having 1 to 15 carbon atoms and optionally having a hydroxy group, a carbonyl group, an ester bond, or an ether bond; $R_2$ and $R_3$ represent a heterocyclic ring having 7 or less carbon atoms in which $R_2$ and $R_3$ are linked to each other, and the heterocyclic ring is a pyrrole ring, a morpholine ring, a thiazine ring, a piperidine ring, a hexamethyleneimine ring, or an azepine ring; each $R_4$ independently represents a hydrogen atom, or a monovalent organic group having 1 to 30 carbon atoms and optionally containing an oxygen atom; and n represents an integer of 1 to 3, wherein, in the formula (3), each $R_1$ independently represents a hydrogen atom, or a monovalent or n-valent organic group having 1 to 15 carbon atoms and optionally having a hydroxy group, a carbonyl group, an ester bond, or an ether bond; $R_2$ and $R_3$ each independently represent an unsubstituted or substituted alkyl group having 1 to 12 carbon atoms, aryl group, aralkyl group, or heterocyclic ring having 7 or less carbon atoms in which $R_2$ and $R_3$ are linked to each other; each $R_4$ independently represents a hydrogen atom, or a monovalent or n-valent organic group having 1 to 30 carbon atoms and optionally containing an oxygen atom; and n represents an integer of 1 to 3.

2. The aminimide compound according to claim 1, wherein the $R_1$ in the formula (1) or (3) is a group represented by the following formula (4) or (5):

(4)

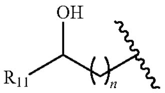

(5)

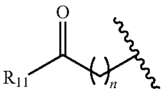

wherein each $R_{11}$ independently represents an alkyl group having 1 to 5 carbon atoms, an alkoxy group having 1 to 5 carbon atoms, an aryl group, or an aralkyl group having 7 to 9 carbon atoms, and each n independently represents an integer of 0 to 6.

3. The aminimide compound according to claim 1, wherein the $R_1$ in the formula (2) is a group represented by the following formula (6) or (7):

(6)

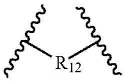

(7)

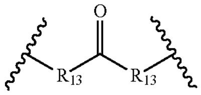

wherein $R_{12}$ and $R_{13}$ each independently represent a single bond, an alkyl group having 1 to 5 carbon atoms, an aryl group, or an aralkyl group having 7 to 9 carbon atoms.

4. The aminimide compound according to claim 1, wherein at least one of $R_2$ and $R_3$ represents an aralkyl group.

5. The aminimide compound according to claim 1, wherein the heterocyclic ring having 7 or less carbon atoms in which $R_2$ and $R_3$ are linked to each other is a heterocyclic ring formed by $R_{23}$ and $N^+$ in the formula (1), (2) or (3) and represented by the following formula (8):

(8)

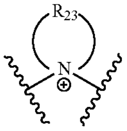

wherein $R_{23}$ represents a group that forms a heterocyclic structure together with $N^+$.

6. The aminimide compound according to claim 1, wherein the $R_4$ in the formula (1) or (2) is a linear or branched alkyl group having 3 to 12 carbon atoms, or a linear or branched alkenyl group having 3 to 6 carbon atoms.

7. The aminimide compound according to claim 1, wherein the $R_4$ in the formula (3) is a group represented by the following formula (9) or (10):

(9)

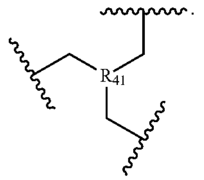

(10)

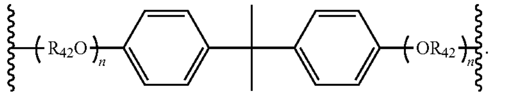

wherein $R_{41}$ and $R_{42}$ each independently represent an alkyl group having 1 to 5 carbon atoms, an aryl group, or an aralkyl group, and each n independently represents an integer of 0 to 10.

8. The aminimide compound according to claim 1, wherein the aminimide compound is represented by the formula (2) or (3) wherein n is 2 or 3.

9. The aminimide compound according to claim 1, wherein the aminimide compound is represented by the formula (2) or (3) wherein n is 2.

10. The aminimide compound according to claim 1, wherein a viscosity at 25° C. is 1300 Pa·s or less.

11. The aminimide compound according to claim 1, wherein a difference ($T_{peak}$-$T_{onset}$) between a peak top temperature ($T_{peak}$) and an onset temperature ($T_{onset}$) of an exothermic peak related to the decomposition of the N—N bond in differential thermal analysis is 45° C. or less.

12. An aminimide composition comprising a plurality of aminimide compounds according to claim 1.

13. The aminimide composition according to claim 12, comprising aminimide compounds represented by the formula (1) and the formula (3).

14. A curing agent comprising an aminimide compound according to claim 1.

15. An epoxy resin composition comprising epoxy resin (α), and a curing agent (β) according to claim 14.

16. The epoxy resin composition according to claim 15, wherein a content of the curing agent (β) is 1 to 50 parts by mass per 100 parts by mass of the epoxy resin (α).

17. The epoxy resin composition according to claim 15, further comprising an acid anhydride-based curing agent (γ).

18. A method for producing an aminimide compound according to claim 1, comprising a reaction step of reacting a carboxylic acid ester compound (A), a hydrazine compound (B), and a glycidyl ether compound (C) under conditions sufficient to form the aminimide compound represented by formula (1), (2), or (3).

19. An encapsulant which is a cured product of an epoxy resin composition according to claim 15.

20. An adhesive comprising an epoxy resin composition according to claim 15, wherein the curing agent (β) comprises an aminimide compound represented by the formula (3).

* * * * *